United States Patent
Michelson

(10) Patent No.: US 6,210,412 B1
(45) Date of Patent: Apr. 3, 2001

(54) METHOD FOR INSERTING FRUSTO-CONICAL INTERBODY SPINAL FUSION IMPLANTS

(76) Inventor: Gary Karlin Michelson, 438 Sherman Canal, Venice, CA (US) 90291

(*) Notice: Subject to any disclaimer, the term of this patent is extended or adjusted under 35 U.S.C. 154(b) by 0 days.

(21) Appl. No.: 08/480,904

(22) Filed: Jun. 7, 1995

Related U.S. Application Data

(63) Continuation-in-part of application No. 08/396,414, filed on Feb. 27, 1995, which is a continuation-in-part of application No. 08/074,781, filed on Jun. 10, 1993, now Pat. No. 5,484,437, which is a continuation-in-part of application No. 07/968,240, filed on Oct. 29, 1992, now Pat. No. 5,741,253, which is a continuation of application No. 07/698,674, filed on May 10, 1991, now abandoned, which is a division of application No. 07/205,935, filed on Jun. 13, 1988, now Pat. No. 5,015,247, and a continuation-in-part of application No. 08/390,131, filed on Feb. 17, 1995, now Pat. No. 5,593,409, and a continuation-in-part of application No. 29/023,623, filed on May 27, 1994, now Pat. No. Des. 377,093.

(51) Int. Cl.⁷ .................................................. A61B 17/56
(52) U.S. Cl. ................................................ 606/61; 623/17
(58) Field of Search ................................. 606/61, 72–78; 623/16, 17, 18

(56) References Cited

U.S. PATENT DOCUMENTS

| Re. 31,865 | 4/1985 | Roux . |
|---|---|---|
| Re. 34,871 | 3/1995 | McGuire et al. . |
| D. 245,259 | 8/1977 | Shen . |
| D. 257,511 | 11/1980 | Zahn . |
| D. 260,525 | 9/1981 | Lassiter . |
| D. 281,814 | 12/1985 | Pratt et al. . |
| 350,420 | 10/1886 | Dillon . |
| D. 397,439 | 8/1998 | Koros et al. . |
| 1,137,585 | 4/1915 | Craig . |
| 2,065,659 | 12/1936 | Cullen . |
| 2,181,746 | 11/1939 | Siebrandt . |
| 2,243,718 | 5/1941 | Moreira . |
| 2,372,622 | 3/1945 | Fassio . |
| 2,514,665 | 7/1950 | Myller . |
| 2,537,070 | 1/1951 | Longfellow . |
| 2,543,780 | 3/1951 | Hipps et al. . |
| 2,677,369 | 5/1954 | Knowles . |
| 2,774,350 | 12/1956 | Cleveland . |
| 2,789,558 | 4/1957 | Rush . |
| 2,832,343 | 4/1958 | Mose . |
| 2,842,131 | 7/1958 | Smith . |
| 2,878,809 | 3/1959 | Treace . |
| 3,128,768 | 4/1964 | Geistauts . |
| 3,298,372 | 1/1967 | Feinberg . |
| 3,426,364 | 2/1969 | Lumb . |
| 3,486,505 | 12/1969 | Morrison . |
| 3,604,487 | 9/1971 | Gilbert . |
| 3,605,123 | 9/1971 | Hahn . |

(List continued on next page.)

FOREIGN PATENT DOCUMENTS

| 1961531 | 7/1970 | (DE) . |
|---|---|---|
| 24 46 039 | 4/1975 | (DE) . |
| 3101333 A1 | 12/1981 | (DE) . |

(List continued on next page.)

OTHER PUBLICATIONS

Adams, et al.; Outline of Orthopaedics, Eleventh Edition; Trunk and Spine, p. 194.
Herkowitz, et al.; Principles of Bone Fusion; The Spine, Third Edition; Chapter 44, p. 1739.
Muschler, et al.; The Biology of Spinal Fusion; Spinal Fusion Science and Technique, Cotler and Cotler, pp. 9–13.

(List continued on next page.)

Primary Examiner—Michael A. Brown
(74) Attorney, Agent, or Firm—Loeb & Loeb LLP

(57) ABSTRACT

The present invention is directed to a method of inserting a variety of interbody spinal fusion implants having at least a partially frusto-conical configuration and the instrumentation and methods by which the implants.

92 Claims, 16 Drawing Sheets

U.S. PATENT DOCUMENTS

| | | |
|---|---|---|
| 3,618,611 | 11/1971 | Urban . |
| 3,709,219 | 1/1973 | Halloran . |
| 3,720,959 | 3/1973 | Hahn . |
| 3,750,652 | 8/1973 | Sherwin . |
| 3,848,601 * | 11/1974 | Ma ......................................... 623/17 |
| 3,855,638 | 12/1974 | Pillar . |
| 3,867,728 | 2/1975 | Stubstad et al. . |
| 3,867,950 | 2/1975 | Fischell . |
| 3,875,595 | 4/1975 | Froning . |
| 3,888,260 | 6/1975 | Fischell . |
| 3,892,232 | 7/1975 | Neufeld . |
| 3,905,047 | 9/1975 | Long . |
| 3,915,151 | 10/1975 | Kraus . |
| 3,916,907 | 11/1975 | Peterson . |
| 3,918,440 | 11/1975 | Kraus . |
| 3,942,535 | 3/1976 | Schulman . |
| 3,948,262 | 4/1976 | Zaffaroni . |
| 3,952,334 | 4/1976 | Bokros et al. . |
| 3,987,499 | 10/1976 | Scharbach et al. . |
| 4,016,651 | 4/1977 | Kawahara et al. . |
| 4,027,392 | 6/1977 | Sawyer et al. . |
| 4,051,905 | 10/1977 | Kleine . |
| 4,059,115 | 11/1977 | Jumashev et al. . |
| 4,070,514 | 1/1978 | Entherly et al. . |
| 4,082,097 | 4/1978 | Mann et al. . |
| 4,086,701 | 5/1978 | Kawahara et al. . |
| 4,124,026 | 11/1978 | Berner et al. . |
| 4,142,517 | 3/1979 | Stravropoulos et al. . |
| 4,168,326 | 9/1979 | Broemer et al. . |
| 4,175,555 | 11/1979 | Herbert . |
| 4,177,524 | 12/1979 | Grell et al. . |
| 4,181,457 | 1/1980 | Holmes . |
| 4,197,850 | 4/1980 | Schulman et al. . |
| 4,206,516 | 6/1980 | Pilliar . |
| 4,222,128 | 9/1980 | Tomonaga et al. . |
| 4,232,679 | 11/1980 | Schulman . |
| 4,237,948 | 12/1980 | Jones et al. . |
| 4,258,716 | 3/1981 | Sutherland . |
| 4,259,072 | 3/1981 | Hirabayashi et al. . |
| 4,262,369 | 4/1981 | Roux . |
| 4,271,832 | 6/1981 | Evans et al. . |
| 4,289,123 | 9/1981 | Dunn . |
| 4,293,962 | 10/1981 | Fuson . |
| 4,309,777 | 1/1982 | Patil . |
| 4,328,593 | 5/1982 | Sutter et al. . |
| 4,333,469 | 6/1982 | Jeffcoat et al. . |
| 4,341,206 | 7/1982 | Perrett et al. . |
| 4,349,921 | 9/1982 | Kuntz . |
| 4,356,572 | 11/1982 | Guillemin et al. . |
| 4,401,112 | 8/1983 | Rezaian . |
| 4,405,319 | 9/1983 | Cosentino . |
| 4,414,979 | 11/1983 | Hirshorn et al. . |
| 4,423,721 | 1/1984 | Otte et al. . |
| 4,439,152 | 3/1984 | Small . |
| 4,450,834 | 5/1984 | Fischer . |
| 4,484,570 | 11/1984 | Sutter et al. . |
| 4,492,226 | 1/1985 | Belykh et al. . |
| 4,497,320 | 2/1985 | Nicholson et al. . |
| 4,501,269 | 2/1985 | Bagby . |
| 4,507,115 | 3/1985 | Kambara et al. . |
| 4,530,360 | 7/1985 | Duarte . |
| 4,535,374 | 8/1985 | Anderson et al. . |
| 4,535,485 | 8/1985 | Ashman et al. . |
| 4,542,539 | 9/1985 | Rowe, Jr. et al. . |
| 4,545,374 | 10/1985 | Jacobson . |
| 4,547,390 | 10/1985 | Ashman et al. . |
| 4,549,547 | 10/1985 | Brighton et al. . |
| 4,552,200 | 11/1985 | Sinha et al. . |
| 4,553,273 | 11/1985 | Wu . |
| 4,554,914 | 11/1985 | Kapp et al. . |
| 4,570,623 | 2/1986 | Ellison et al. . |
| 4,570,624 | 2/1986 | Wu . |
| 4,592,346 | 6/1986 | Jurgutis . |
| 4,599,086 | 7/1986 | Doty . |
| 4,600,000 | 7/1986 | Edwards . |
| 4,602,638 | 7/1986 | Adams . |
| 4,604,995 | 8/1986 | Stephens . |
| 4,608,052 | 8/1986 | Van Kampen et al. . |
| 4,611,581 | 9/1986 | Steffee . |
| 4,619,264 | 10/1986 | Singh . |
| 4,628,921 | 12/1986 | Rousso . |
| 4,634,720 | 1/1987 | Dorman et al. . |
| 4,636,217 | 1/1987 | Ogilvie et al. . |
| 4,636,526 | 1/1987 | Dorman et al. . |
| 4,645,503 | 2/1987 | Lin et al. . |
| 4,653,486 | 3/1987 | Coker . |
| 4,655,777 | 4/1987 | Dunn . |
| 4,661,536 | 4/1987 | Dorman et al. . |
| 4,664,567 | 5/1987 | Edwards . |
| 4,665,920 | 5/1987 | Campbell . |
| 4,677,883 | 7/1987 | Lee . |
| 4,677,972 | 7/1987 | Tornier . |
| 4,693,721 | 9/1987 | Ducheyne . |
| 4,696,290 | 9/1987 | Steffee . |
| 4,698,375 | 10/1987 | Dorman et al. . |
| 4,710,075 | 12/1987 | Davison . |
| 4,713,004 | 12/1987 | Linkow et al. . |
| 4,714,469 | 12/1987 | Kenna . |
| 4,721,103 | 1/1988 | Freedland . |
| 4,736,738 | 4/1988 | Lipovsek et al. . |
| 4,743,256 | 5/1988 | Brantigan . |
| 4,743,260 | 5/1988 | Burton . |
| 4,759,766 | 7/1988 | Buettner-Janz et al. . |
| 4,759,769 | 7/1988 | Hedman et al. . |
| 4,769,881 | 9/1988 | Pedigo et al. . |
| 4,781,591 | 11/1988 | Allen . |
| 4,790,303 | 12/1988 | Steffee . |
| 4,805,602 | 2/1989 | Puno et al. . |
| 4,820,305 | 4/1989 | Harms et al. . |
| 4,830,000 | 5/1989 | Shutt . |
| 4,834,757 * | 5/1989 | Brantigan ............................... 623/17 |
| 4,848,327 | 7/1989 | Perdue . |
| 4,851,008 | 7/1989 | Johnson . |
| 4,863,476 | 9/1989 | Shepperd . |
| 4,863,477 | 9/1989 | Monson . |
| 4,865,603 | 9/1989 | Noiles . |
| 4,877,020 | 10/1989 | Vich . |
| 4,878,915 * | 11/1989 | Brantigan ............................... 623/17 |
| 4,903,882 | 2/1990 | Long . |
| 4,904,260 | 2/1990 | Ray et al. . |
| 4,904,261 * | 2/1990 | Dove ....................................... 623/17 |
| 4,911,718 | 3/1990 | Lee et al. . |
| 4,913,144 | 4/1990 | Del Medico . |
| 4,936,848 | 6/1990 | Babgy . |
| 4,943,291 | 7/1990 | Tanguy . |
| 4,955,885 | 9/1990 | Meyers . |
| 4,955,908 | 9/1990 | Frey et al. . |
| 4,957,495 | 9/1990 | Kluger . |
| 4,960,420 | 10/1990 | Goble et al. . |
| 4,961,740 | 10/1990 | Ray et al. . |
| 4,968,316 | 11/1990 | Hergenroeder . |
| 4,969,888 | 11/1990 | Scholten et al. . |
| 4,987,904 | 1/1991 | Wilson . |
| 5,015,247 | 5/1991 | Michelson . |
| 5,015,255 | 5/1991 | Kuslich . |
| 5,026,373 | 6/1991 | Ray et al. . |
| 5,030,236 | 7/1991 | Dean . |
| 5,055,104 | 10/1991 | Ray . |
| 5,059,193 | 10/1991 | Kuslich . |
| 5,062,845 | 11/1991 | Kuslich et al. . |
| 5,071,437 | 12/1991 | Steffee . |

| | | |
|---|---|---|
| 5,084,050 | 1/1992 | Draenert . |
| 5,102,414 | 4/1992 | Kirsch . |
| 5,108,422 | 4/1992 | Green et al. . |
| 5,112,336 | 5/1992 | Krevolin et al. . |
| 5,116,304 | 5/1992 | Cadwell . |
| 5,122,130 | 6/1992 | Keller . |
| 5,123,926 | 6/1992 | Pisharodi . |
| 5,171,278 | 12/1992 | Pisharodi . |
| 5,192,327 | 3/1993 | Brantigan . |
| 5,246,458 | 9/1993 | Graham . |
| 5,258,031 | 11/1993 | Salib et al. . |
| 5,263,953 | 11/1993 | Bagby . |
| 5,292,252 | 3/1994 | Nickerson et al. . |
| 5,306,309 | 4/1994 | Wagner et al. . |
| 5,314,427 | 5/1994 | Goble et al. . |
| 5,324,295 | 6/1994 | Shapiro . |
| 5,352,229 | 10/1994 | Goble et al. . |
| 5,360,430 | 11/1994 | Lin . |
| 5,364,399 | 11/1994 | Lowery et al. . |
| 5,370,662 | 12/1994 | Stone et al. . |
| 5,370,697 | 12/1994 | Baumgartner . |
| 5,393,036 | 2/1995 | Sheridan . |
| 5,396,880 | 3/1995 | Kagan et al. . |
| 5,397,364 | 3/1995 | Kozak et al. . |
| 5,425,772 | 6/1995 | Brantigan . |
| 5,435,723 | 7/1995 | O'Brien . |
| 5,443,514 | 8/1995 | Steffee . |
| 5,458,638 | 10/1995 | Kuslich et al. . |
| 5,489,307 | 2/1996 | Kuslich et al. . |
| 5,489,308 | 2/1996 | Kuslich et al. . |
| 5,571,109 | 11/1996 | Bertagnoli . |
| 5,669,909 | 9/1997 | Zdeblick et al. . |
| 5,683,463 | 11/1997 | Godefroy et al. . |
| 5,766,252 | 6/1998 | Henry et al. . |
| 5,906,616 | 5/1999 | Pavlov et al. . |
| B1 4,232,679 | 5/1988 | Schulman . |

FOREIGN PATENT DOCUMENTS

| | | |
|---|---|---|
| 3132520 A1 | 6/1982 | (DE) . |
| 3505567 A1 | 6/1986 | (DE) . |
| 36 08 163 A1 | 9/1987 | (DE) . |
| 41 04 359 A1 | 8/1992 | (DE) . |
| 0 077 159 | 4/1983 | (EP) . |
| 0 162 005 | 11/1985 | (EP) . |
| 0 260 044 | 3/1988 | (EP) . |
| 0303241 A2 | 2/1989 | (EP) . |
| 0 307 241 | 3/1989 | (EP) . |
| 0499465 A1 | 8/1992 | (EP) . |
| 0551187 A1 | 7/1993 | (EP) . |
| 0577179 A1 | 1/1994 | (EP) . |
| 0 599 419 A2 | 6/1994 | (EP) . |
| 283078 | 5/1985 | (ES) . |
| 2 295 729 | 7/1976 | (FR) . |
| 0 179 695 | 4/1986 | (FR) . |
| 2 581 336 | 11/1986 | (FR) . |
| 2 703 580 | 10/1994 | (FR) . |
| 2076657 | 12/1981 | (GB) . |
| 2082754 | 3/1982 | (GB) . |
| 2126094 | 3/1984 | (GB) . |
| 2164277 | 3/1986 | (GB) . |
| 57-29348 | 2/1982 | (JP) . |
| 60-31706 | 2/1985 | (JP) . |
| 60-43984 | 3/1985 | (JP) . |
| 61-122859 | 6/1986 | (JP) . |
| 62-155846 | 7/1987 | (JP) . |
| 106 101 | 7/1939 | (SE) . |
| 1107854 | 8/1984 | (SU) . |
| 1124960 | 11/1984 | (SU) . |
| 1217374 | 3/1986 | (SU) . |
| 1222254 | 4/1986 | (SU) . |
| 84/01298 | 4/1984 | (WO) . |
| 91/06266 | 5/1991 | (WO) . |
| 92/14423 | 9/1992 | (WO) . |
| 93/01771 | 2/1993 | (WO) . |

OTHER PUBLICATIONS

Zindrick, et al.; Lumbar Spine Fusion: Different Types and Indications; The Lumbar Spine, vol. 1, Second Edition, pp. 588–593 (1996).

Gillingham, F.J., et al.; Automatic Patient Monitoring in the Ward; Brit. J. Surg., vol. 53, No. 10, pp. 864–866 (Oct. 1966).

Maloney, A.F.J., et al.; Clinical and Pathological Observations in Fatal Head Injuries, Brit. J. Surg., vol. 56, No. 1, pp. 23–31 (Jan. 1969).

Harris, P., et al.; Spinal Deformity After Spinal Cord Injury; Paraplegia, vol. 6, No. 4, pp. 232–238 (Feb. 1969).

Gillingham, F.J., et al.; Head injuries; Proceedings of the 18$^{th}$ World Congress of the International College of Surgeons, Rome, pp. 68–71 (May 28–31, 1972).

Whatmore, W. J.; Sincipital Encephalomeningoceles; Brit. J. Surg., vol. 60, No. 4, pp. 261–270 (Apr. 1973).

Whatmore, W. J.; Meningioma Following Trauma; Brit. J. Surg., vol. 60, No. 6, pp. 496–498 (Jun. 1973).

Bagby, George W.; Wobbler Syndrome in Horses (the Ataxic Horse); Spokane County Medical Society Bulletin; Spring 1979.

Rathke, F.W., et al.; Surgery of the Spine; Atlas of Orthopaedic Operations, vol. 1, p. 137, W.B. Saunders Co., Philadelphia (1979).

Albrektsson, T., et al.; Osseointegrated Titanium Implants; Acta. Orthop. Scand.; vol. 52:155–170 (1981).

Raveh, J., et al.; Neue Rekonstruktionsmoglichkeiten des Unterkiefers bei knochernen Defekten nach Tumorresektionen; Der Chirurg vol. 53:459–467 (1982).

Crock, H. V.; Practice of Spinal Surgery; Springer–Verlag/Wien, New York (1983).

DeBowes, R.M., et al.; Study of Bovine . . . Steel Baskets; Transactions of the 29th Annual Meeting; Orthopaedic Research Society, vol. 8, p. 407, Mar. 8–10 (1983).

O'Neill, P., et al.; Spinal Meningoceles in Association with Neurofibromatosis; Neurosurgery, vol. 13, No. 1, pp. 82–84 (Jul. 1983).

Brandt, L., et al.; A Dowel Inserter for Anterior Cervical Interbody Fusion; J. Neurosurg. 61:793–794 (Oct. 1984).

Whatmore, W.J., et al.; The Coventry Cervical Spreader and Dowel Inserter; ACTA Neurochirurgica, vol. 70, FASC. 1–2 (1984).

Raveh, J., et al.; Use of the Titanium–coated Hollow Screw and Reconstruction Plate System in Bridging of Lower Jaw Defects; J. Oral Maxillofac Surg. 42:281–294 (1984).

Otero–Vich, Jose M.; Anterior Cervical Interbody Fusion with Threaded Cylindrical Bone; J. Neurosurg 63:750–753 (Nov. 1985).

Morscher, E., et al.; Die vordere Verplattung der Halswirbelsäule mit dem Hohlschrauben–Plattensystem aus Titanium, Der Chirurg, vol. 57, pp. 702–707 (1986) with English Translation.

Bagby, G.W.; Basket Implant Facilitates Spinal Fusion; Orthopedics Today, vol. 7, No. 10, (Oct. 1987).

Butts, M. K., et al.; Biomechanical Analysis of a New Method for Spinal Interbody Fixation; 1987 Symposium, American Society of Mechanical Engineers, "Advances in Bioengineering", Boston, MA (Dec. 13–18, 1987).

Crawley et al.; A Modified Cloward's Technique for Arthrodesis of the Normal Metacarpophalangeal Joint in the Horse; Veterinary Surgery, vol. 17, No. 3, pp. 117–127 (1988).

Raveh, J., et al.; Surgical Procedures for Reconstruction of the Lower Jaw Using the Titanium–Coated Hollow–Screw Reconstruction Plate System: Bridging of Defects; Otolaryngologic Clinics of North America; vol. 20, No. 3 (Aug. 1987).

Whatmore, W. J.; Proceedings of the Society of British Neurological Surgeons; Journal of Neurology, Neurosurgery, and Psychiatry, 50:1093–1100 (1987).

Goldthwaite, N., et al.; Toward Percutaneous Spine Fusion; Ch. 45; Lumbar Spine Surgery; C.V. Mosby Company, pp. 512–522 (1987).

Bagby, G.W.; Arthrodesis by the Distraction–Compression Method Using a Stainless Steel Implant; Orthopedics, vol. II, No. 6, pp. 931–34 (Jun. 1987).

Itoman, M., et al.; Banked Bone Grafting for Bone Defect Repair—Clinical Evaluation of Bone Union and Graft Incorporation; J. Jpn. Orthop. Assoc. 62:461–469 (1988).

Kane, W.J.; Direct Current Electrical Bone Growth Stimulation for Spinal Fusion; Spine, vol. 13, No. 3, pp. 363–365 (Mar. 1988).

The SpF–T Spinal Fusion Stimulator: An Efficacious Adjunct that Meets the Diverse Needs of Spine Patients; EBI Medical Systems; (Aug. 1991).

Schmitz et al.; Performance of Alloplastic Materials and Design of an Artificial Disc; The Artificial Disc, Brock, Mayer, Weigel; pp. 23–34 (1991).

The Use of Direct Current for Electrically Induced Osteogenesis; The Positive Effect of an Electronegative charge on Bone Growth; EBI Medical Systems (Feb. 1993).

Mylonas, C., et al.; Anterior Cervical Decompression and Fusion Using the Coventry Cervical Spreader and Dowel Inserter; British Journal of Neurosurgery, 7:545–549 (1993).

Fusion of the Lumbar Spine; Anterior Monosegmental Fusion L5–S1, Atlas of Spinal Operations, Thieme, pp. 270–274 (1993).

Spine Basics, Danek Group, Inc., Glossary (1993).

Lumbar Spine Surgery, Techniques & Complications; History of Lumbar Spine Surgery (1994) pp. 11–15; 27; 30; 35–45; 265–268.

*Practice Of Spinal Surgery*, Crock, Henry V., pp. 79–83, Springer–Verlag (1983).

* cited by examiner

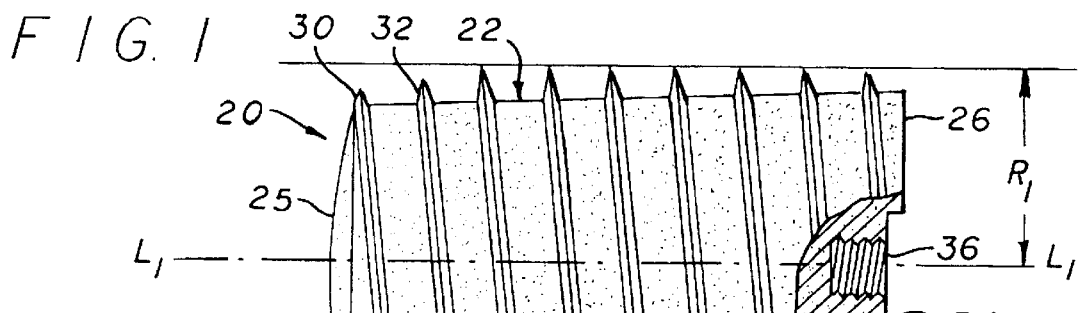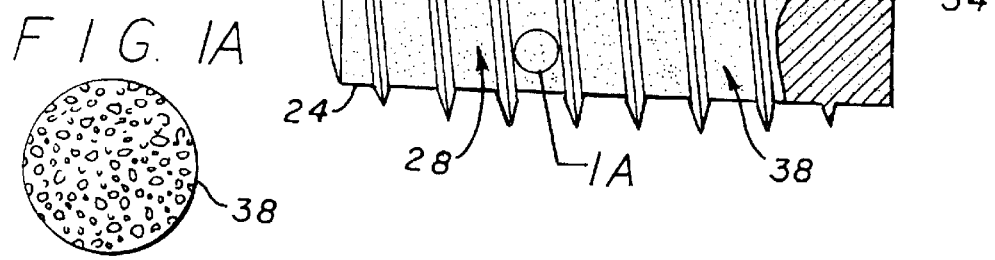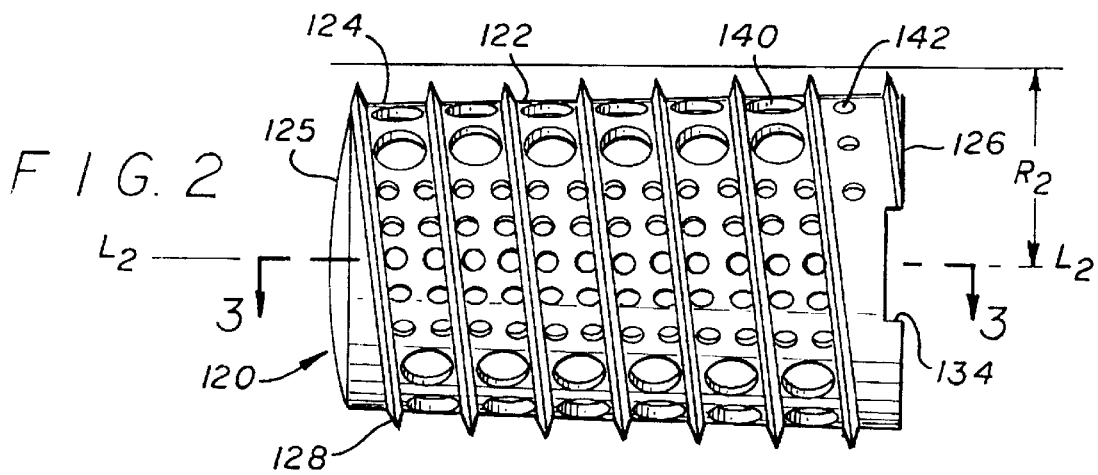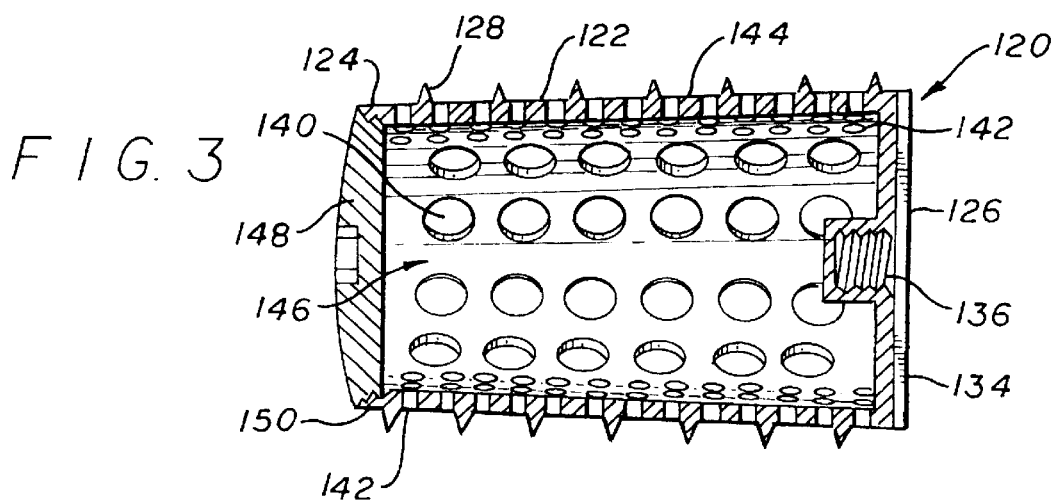

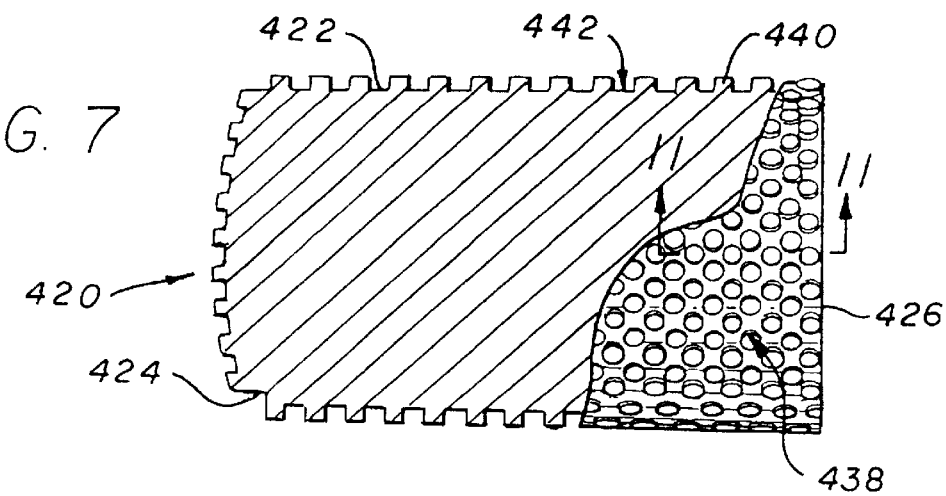
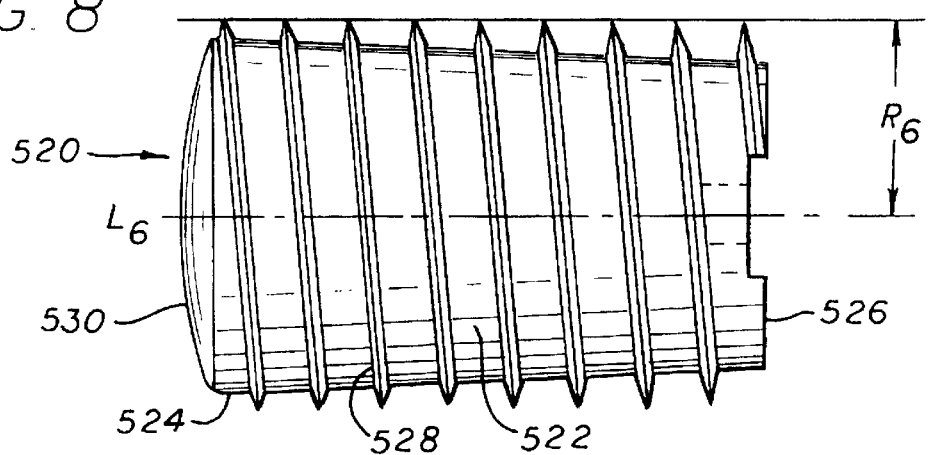
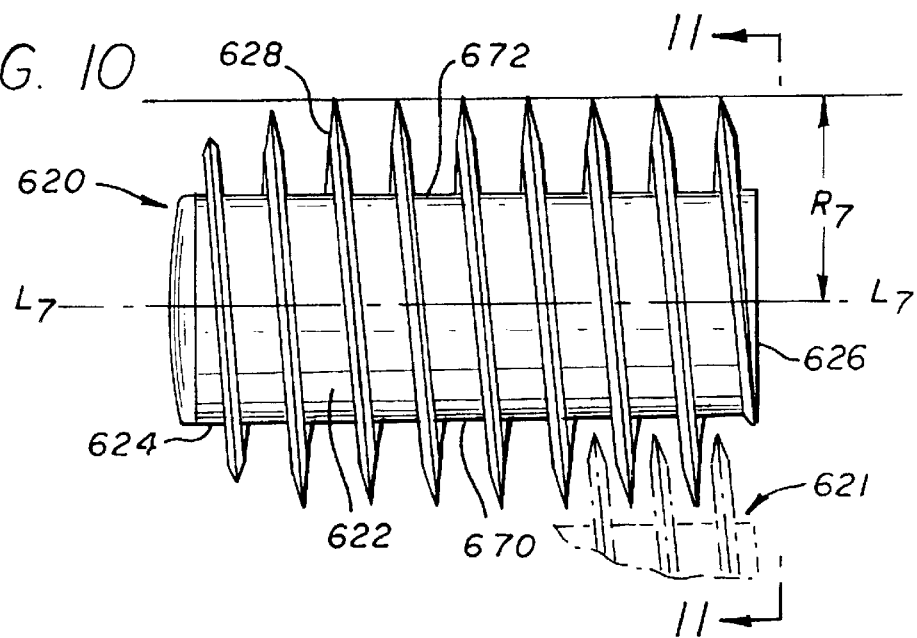

FIG. 19
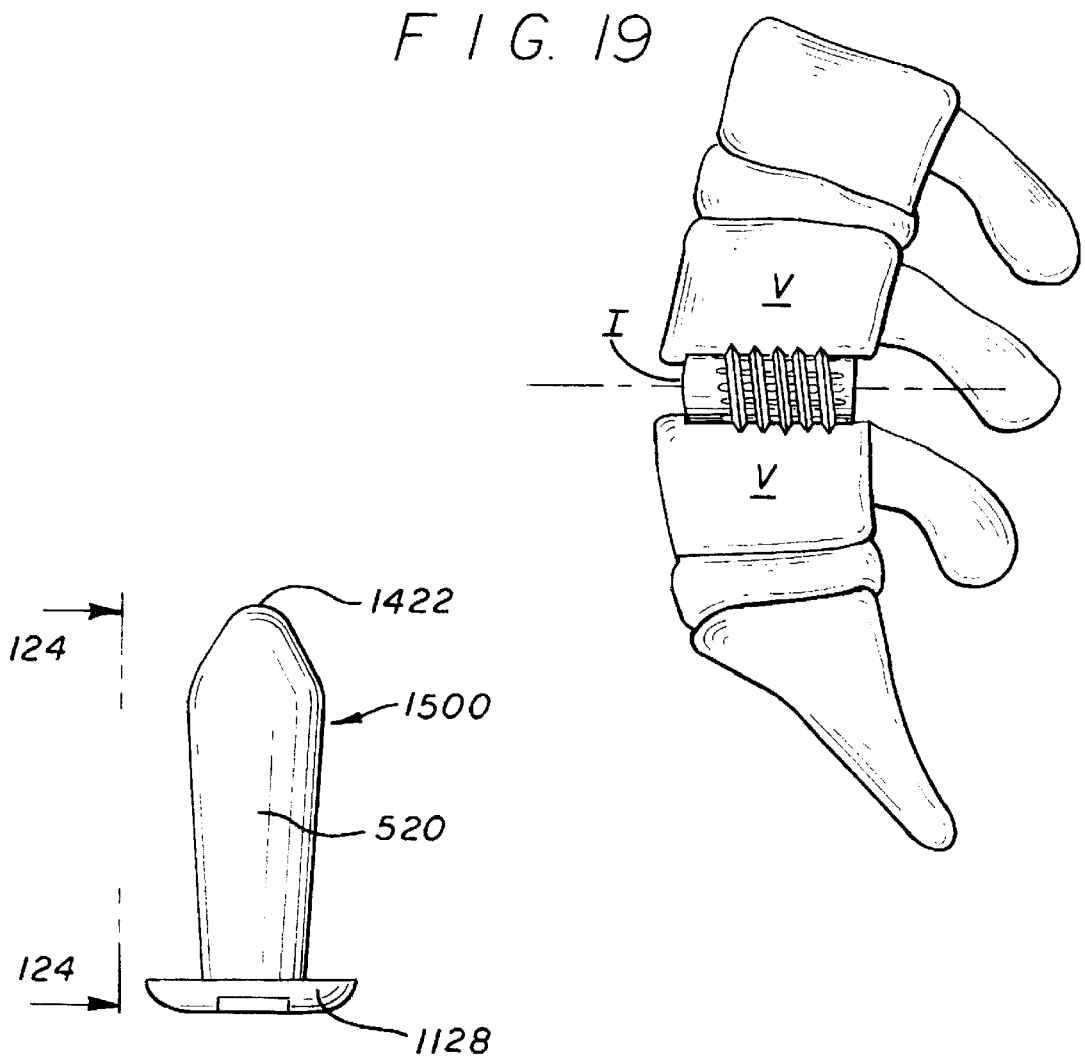
FIG. 20
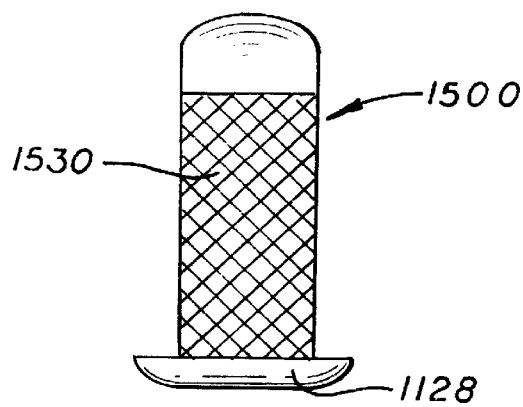
FIG. 21

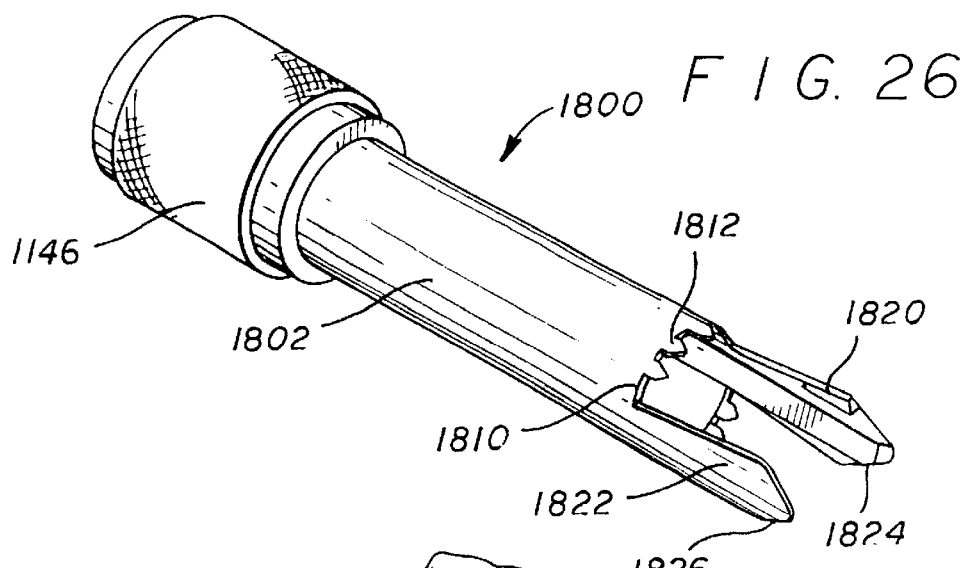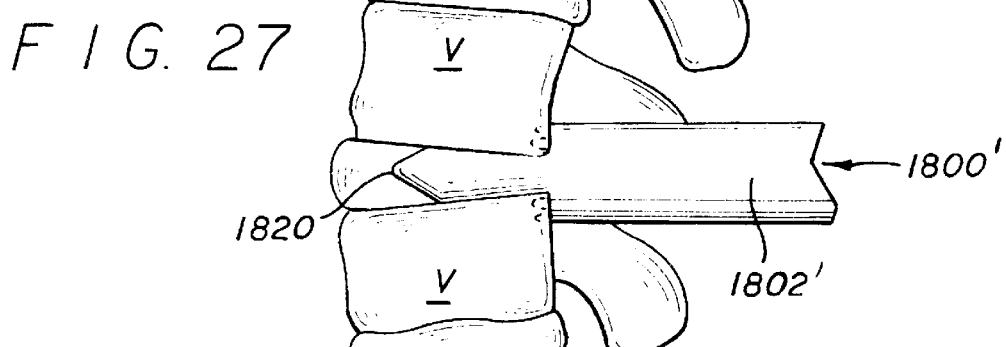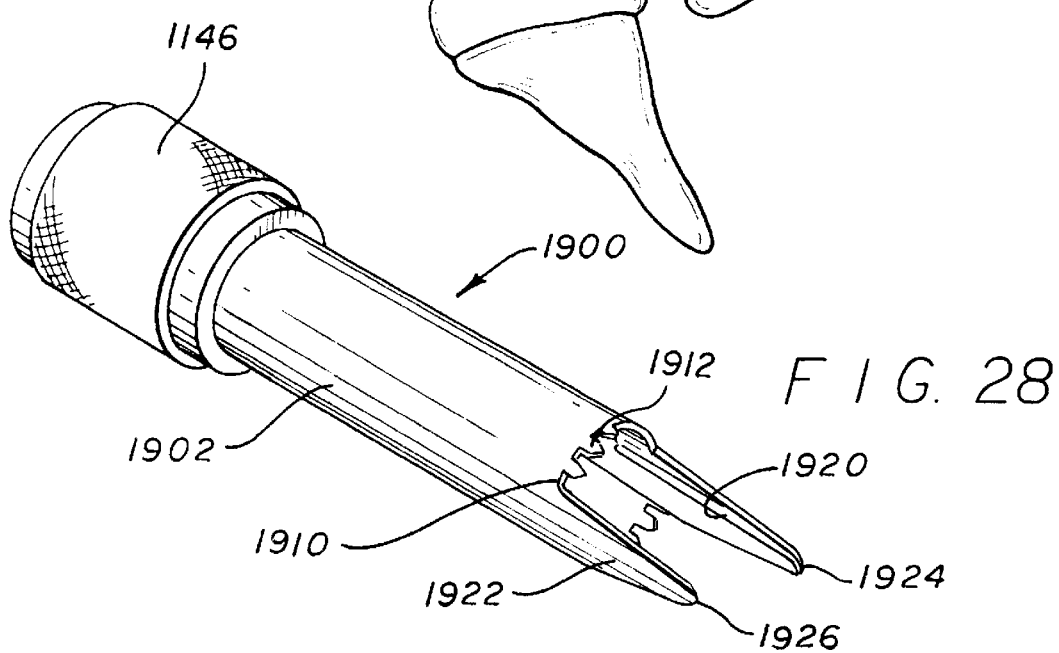

METHOD FOR INSERTING FRUSTO-CONICAL INTERBODY SPINAL FUSION IMPLANTS

RELATED APPLICATIONS

This application is a continuation in part of U.S. application Ser. No. 08/396,414 filed on Feb. 27, 1995 which is a continuation-in-part of U.S. application Ser. No. 08/074,781 filed on Jun. 10, 1993, now U.S. Pat. No. 5,484,437, which is a continuation in part of U.S. application Ser. No. 07/968,240 filed on Oct. 29, 1992, now U.S. Pat. No. 5,741,253 which is a continuation of U.S. application Ser. No. 07/698,674 filed on May 10, 1991, now abandoned which is a divisional of application Ser. No. 07/205,935 filed on Jun. 13, 1988, now U.S. Pat. No. 5,015,247 all of which are incorporated herein by reference.

This application is also a continuation-in-part of U.S. application Ser. No. 08/390,131 entitled Interbody Spinal Fusion Implants filed on Feb. 17, 1995, now U.S. Pat. No. 5,593,409. This application is also a continuation in part of design patent application Ser. No. 29/023,623 entitled Spinal Distractor filed on May 27, 1994, now U.S. Pat. No. Des. 377,093.

BACKGROUND OF THE INVENTION

1. Field of the Invention

The present invention relates generally to a method for inserting interbody spinal fusion implants, and in particular to a method for inserting spinal fusion implants configured to restore and maintain two adjacent vertebrae of the spine in anatomical lordosis.

2. Description of the Related Art

Interbody spinal fusion refers to the method of achieving bony bridging between adjacent vertebrae through the disc space, the space between adjacent vertebrae normally occupied by a spinal disc. Numerous implants to facilitate such a fusion have been described by Cloward, Brantigan, and others, and are known to those skilled in the art. Generally, cylindrical implants offer the advantage of conforming to an easily prepared recipient bore spanning the disc space and penetrating into each of the adjacent vertebrae. Such a bore may be created by use of a drill. It is an anatomical fact that both the cervical spine and the lumbar spine are normally lordotic, that is convex forward. Such alignment is important to the proper functioning of the spine. Commonly, those conditions which require treatment by spinal fusion are associated with a loss of lordosis.

Michelson, in U.S. patent application Ser. No. 08/396, 414, entitled APPARATUS AND METHOD OF INSERTING SPINAL IMPLANTS, teaches a method for restoring the anatomical lordosis of the spine while performing the interbody fusion procedure. While this has been a significant advance over prior methods, it has nevertheless been associated with a sometimes less than desirable consequence, that being the uneven removal of bone from each of the adjacent vertebrae relative to the vertebral endplates adjacent the disc space.

Therefore, there exists a need for spinal fusion implants and instrumentation that permits for the uniform depth of bone removal from each of the adjacent vertebrae while restoring anatomical lordosis.

SUMMARY OF THE INVENTION

The present invention is directed to a method for inserting a variety of interbody spinal fusion implants having at least a partially frusto-conical configuration to achieve a desired anatomical lordosis of the spine. In the preferred embodiment of the method of the present invention, the spinal fusion implants being inserted have an outer locus in which at least some of the points of the implant comprise a partially or fully frusto-conical shape substantially along the portion of the implant in contact with the adjacent vertebrae of the spine and have an insertion end and a trailing end. The spinal fusion implants may be further modified so that while the upper and lower surfaces are portions of a frusto-cone, or a cylinder at least one side portion may be truncated to form a planar surface that is parallel to the central longitudinal axis of the implant to form straight walls. These implants may have a more tapered aspect at the insertion end of the implant to facilitate insertion. The spinal fusion implants of the present invention may be relatively solid and/or porous and/or hollow, and may have surface roughenings to promote bone ingrowth and stability.

In the preferred method of the present invention, the diseased disc between two vertebrae is at least partially removed. The two vertebrae adjacent the diseased disc are then optimally distracted and placed in the desired amount of lordosis by any of a number of well known means including, but not limited to, those means that distract the vertebral bodies by engaging screws placed into the anterior aspect of the vertebral bodies, and disc space distractors that are placed from the anterior aspect of the spine into the disc space and are then used to urge the vertebral endplates away from each other and into lordosis. When the correct amount of distraction and lordosis have been achieved at the affected disc level, then a frusto-conical space is created from anterior to posterior between the adjacent vertebrae. The frusto-conical space that is created is greater in diameter than the disc space height, such that some bone is removed from each of the adjacent vertebrae. The created space is generally frusto-conical in shape, being greatest in diameter anteriorly and tapering to a lesser diameter posteriorly.

In an alternative method of implant insertion, the use of at least partially frusto-conical interbody spinal fusion implants allows for the creation of lordosis by the implant itself where none is present to begin with. The disc space which in the preferred circumstance would be fully distracted but need not be, but lacking lordosis, could have a bore drilled across that space such that equal arcs of bone are removed from each of the adjacent vertebrae using a drill or bone milling device capable of producing a cylindrical bore. The vertebrae, whether distracted from each other or not, are essentially lacking the full restoration of lordosis. The use of the substantially cylindrical bone drill provides for the removal of a generally uniform thickness of bone from each of the adjacent vertebrae from anterior to posterior. The insertion of a frusto-conical implant, having a larger diameter at its trailing edge than at its leading edge, then forces the anterior aspects of the adjacent vertebrae apart more so than the posterior aspects where the diameter is lesser. This utilizes the implant to produce the desired lordosis.

To further assist incorporation into the spinal fusion bone mass, the spinal fusion implants of the present invention may have wells extending into the material of the implant from the surface for the purpose of holding fusion promoting materials and to provide for areas of bone ingrowth fixation. These wells, or holes, may pass either into or through the implant and may or may not intersect. The spinal fusion implants of the present invention may have at least one chamber which may be in communication through at least one opening to the surface of the implant. Said chamber may have at least one access opening for loading the chamber with fusion promoting substances. The access opening may be capable of being closed with a cap or similar means. Still further, a variety of surface irregularities may be employed to increase implant stability and implant surface area, and/or for the purpose of advancing the spinal fusion implant into the fusion site such as a thread. The exterior of the spinal fusion implant of the present invention may have wholly or in part, a rough finish, knurling, forward facing ratchetings, threads or other surface irregularities sufficient to achieve the purpose described.

The spinal fusion implants of the present invention offer significant advantages over the prior art implants:

1. Because the spinal fusion implants of the present invention are at least partially frusto-conical in shape, those that taper from the leading edge to the trailing edge they are easy to introduce and easy to fully insert into the spinal segment to be fused. In the preferred embodiment, where the leading edge of the implant is larger than the trailing edge, the implant utilizes a tapered forward portion and an increasing thread height relative to the body from the leading edge to the trailing edge to facilitate insertion.
2. The shape of the implants of the present invention is consistent with the shape of the disc, which the implants at least in part replace, wherein the front of the disc is normally taller than the back of the disc, which allows for normal lordosis. The implants of the present invention are similarly taller anteriorly than they are posteriorly.
3. The spinal fusion implants of the present invention allow for a minimal and uniform removal of bone from the vertebrae adjacent the disc space while still providing for an interbody fusion in lordosis when properly inserted.
4. The spinal fusion implants of the present invention conform to a geometric shape, which shape is readily producible at the site of fusion, to receive said spinal fusion implants.

The spinal fusion implants of the present invention can be made of any material appropriate for human implantation and having the mechanical properties sufficient to be utilized for the intended purpose of spinal fusion, including various metals such as cobalt chrome, stainless steel or titanium including its alloys, various plastics including those which are bio-absorbable, and various ceramics or combination sufficient for the intended purpose. Further, the spinal fusion implants of the present invention may be made of a solid material, a mesh-like material, a porous material and may comprise, wholly or in part, materials capable of directly participating in the spinal fusion process, or be loaded with, composed of, treated or coated with chemical substances such as bone, morphogenic proteins, hydroxyapatite in any of its forms, and osteogenic proteins, to make them bioactive for the purpose of stimulating spinal fusion. The implants of the present invention may be wholly or in part bioabsorbable.

OBJECTS OF THE PRESENT INVENTION

It is an object of the present invention to provide a method for inserting frusto-conical spinal fusion implants into the spine;

It is yet another object of the present invention to provide a method for inserting frusto-conical spinal fusion implants that are capable of maintaining anatomic alignment and lordosis of two adjacent vertebrae during the spinal fusion process;

It is yet another object of the present invention to provide a method for inserting frusto-conical spinal fusion implants that is capable of providing stability between adjacent vertebrae when inserted;

It is further another object of the present invention to provide a method of inserting frusto-conical spinal fusion implants that includes spacing apart and supporting adjacent vertebrae;

It is still further another object of the present invention to provide a method for inserting frusto-conical spinal fusion implants that is consistent in use with the preservation of a uniform thickness of the subchondral vertebral bone;

It is another object of the present invention to provide a method for inserting frusto-conical spinal fusion implants having a shape which conforms to an easily produced complementary bore at the fusion site; and It is a further object of the present invention to provide a method for inserting a frusto-conical spinal fusion implant which may be placed side by side adjacent to a second identical implant across the same disc space, such that the combined width of the two implants is less than sum of the individual heights of each implant.

These and other objects of the present invention will become apparent from a review of the accompanying drawings and the detailed description of the drawings.

BRIEF DESCRIPTION OF THE DRAWINGS

FIG. 1 is a side elevational view of a frusto-conical spinal fusion implant having a body that is frusto-conical with an external thread having a substantially uniform radius.

FIG. 1A is an enlarged fragmentary view along line 1A of FIG. 1 illustrating the surface configuration of the implant of FIG. 1.

FIG. 2 is a side elevational view of an alternative embodiment of the spinal fusion implant having a frusto-conical body with openings through the wall of the body.

FIG. 3 is as cross sectional view along line 3—3 of the implant of FIG. 3A.

FIG. 7 is a side elevational view in partial cut-away of an alternative embodiment of the spinal fusion implant having a body that is frusto-conical and a surface configuration comprising a plurality of spaced apart posts.

FIG. 8 is a side elevational view of an alternative embodiment of the spinal fusion implant of FIG. 1.

FIG. 10 is a side elevational view of an alternative embodiment of the spinal fusion implant having a frusto-conical body and truncated sides.

FIG. 19 is a side elevational view of a spinal implant inserted between two adjacent vertebrae of the spine in which lordosis has been restored.

FIG. 20 is a side elevational view of a Posterior Short Lordotic Distractor of the present invention.

FIG. 21 is a top plan view along lines 21—21 of FIG. 20 of the Posterior Short Lordotic Distractor of the present invention.

FIG. 26 is a perspective side view of a Posterior Lordotic Extended Outer Sleeve of the present invention having uneven extended members for restoring and maintaining lordosis of the spine and engagement means for engaging the vertebrae.

FIG. 27 is a side elevational view of a portion of the Posterior Lordotic Extended Outer Sleeve of FIG. 26 inserted between adjacent vertebrae from the posterior aspect of the spine to restore and maintain lordosis.

FIG. 28 is a perspective side view of an Anterior Lordotic Extended Outer Sleeve of the present invention having extended members for restoring and maintaining lordosis of the spine from the anterior aspect of the spine.

DETAILED DESCRIPTION OF THE DRAWINGS

Figure 3A:
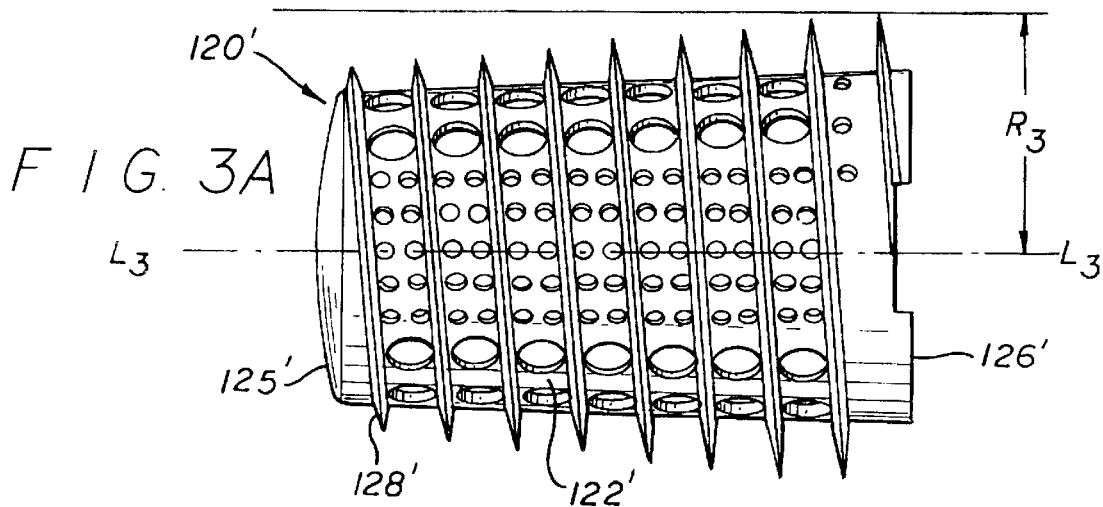
FIG. 3A is an alternative embodiment of the spinal fusion implant having a frusto-conical body with an external thread radius and thread height that are not constant.

The first part of the Detailed Description Of The Drawings is directed to the description of the structure of the frusto-conical implants inserted by the method of the present invention. The second part of the description of the drawings is directed to the method of the present invention.

Frusto-Conical Implants

Referring to FIG. 1, a side elevational view of the spinal fusion implant for insertion with the method of the present invention generally referred to by numeral 20 is shown. The implant 20 has a body 22 that is frusto-conical in shape such that the body 22 has a diameter (root diameter) that is generally frusto-conical. The body 22 has an insertion end 24 and a trailing end 26. The insertion end 24 may include a tapered portion 25 to facilitate insertion of the spinal implant 20. In the preferred embodiment, when the implant 20 is inserted from the anterior aspect of the spine, the body 22 of the implant 20 has a maximum diameter at a point nearest to the trailing end 26 and a minimum diameter at a point nearest to the insertion end 24.

The implant 20 has an external thread 28 having a substantially uniform radius $R_1$ measured from the central longitudinal axis $L_1$ of the implant 20. The outer locus of the external thread 28 (major diameter) has an overall configuration that is substantially parallel to the longitudinal axis $L_1$. While the major diameter of the implant 20 is substantially uniform, the external thread 28 may be modified at the leading edge by having initially a reduced thread radius to facilitate insertion of the implant 20 and may also be modified to make the external thread 28 self-tapping. In the preferred embodiment, the external thread 28 has a first thread 30 of a lesser radius than the radius $R_1$ of the remainder of the external thread 28 to facilitate insertion of the implant 20. The second thread 32 has a greater radius than the first thread 30, but is still shorter than the radius $R_1$ of the remainder of the external thread 28 which is thereafter of constant radius.

The body 22 is frusto-conical substantially along the portion of the body 22 in contact with the adjacent vertebrae of the spine which allows for the creating and maintaining of the adjacent vertebrae of the spine in the appropriate angular relationship to each other in order to preserve and/or restore the normal anatomic lordosis of the spine. The substantially uniform radius $R_1$ of the external thread 28 of the implant 20 allows for the engaging of the bone of the adjacent vertebrae in a position that counters the forces which tend to urge the implant 20 from between the adjacent vertebrae in the direction opposite to which the implant 20 was implanted. The greater thread height measured from the body 22 near the leading end 24 of the implant 20 provides greater purchase into the vertebral bone and again enhances the stability of the implant 20. Further, the configuration of the external thread 28 increases the surface area of the implant 20 in contact with the vertebrae to promote bone ingrowth.

The implant 20 has a recessed slot 34 at its trailing end 26 for receiving and engaging insertion instrumentation for inserting the implant 20. The recessed slot 34 has a threaded opening 36 for threadably attaching the implant 20 to instrumentation used for inserting the implant 20.

Referring to FIG. 1A, the implant 20 has an outer surface 38 that is porous to present an irregular surface to the bone to promote bone ingrowth. The outer surface 38 is also able to hold fusion promoting materials and provides for an increased surface area to engage the bone in the fusion process and to provide further stability. It is appreciated that the outer surface 38, and/or the entire implant 20, may comprise any other porous material or roughened surface sufficient to hold fusion promoting substances and/or allow for bone ingrowth and/or engage the bone during the fusion process. The implant 20 may be further coated with bioactive fusion promoting substances including, but not limited to, hydroxyapatite compounds, osteogenic proteins and bone morphogenic proteins. The implant 20 is shown as being solid, however it is appreciated that it can be made to be substantially hollow or hollow in part.

In the preferred embodiment, for use in the lumbar spine, the implant 20 has an overall length in the range of approximately 24 mm to 32 mm with 26 mm being the preferred length. The body 22 of the implant 20 has a root diameter at the insertion end 24 in the range of 8–20 mm, with 14–16 mm being the preferred root diameter at the insertion end, and a root diameter at the trailing end 26 in the range of 10–24 mm, with 16–18 mm being the preferred diameter at the trailing end 26, when said implants are used in pairs.

When used singly in the lumbar spine, the preferred diameters would be larger.

In the preferred embodiment, the implant 20 has a thread radius $R_1$ in the range of 6 mm to 12 mm, with 9–10 mm being the preferred radius $R_1$. For use in the cervical spine, the implant 20 has an overall length in the range of approximately 10–22 mm, with 12–14 mm being the preferred length. The body 22 of the implant 20 has a root diameter at the insertion end 24 in the range of 8–22 mm, with 16–18 mm being the preferred root diameter at the insertion end when used singly, and 8–10 mm when used in pairs. The body 22 of the implant 20 has a root diameter at the trailing end 26 in the range of 10–24 mm, with 18–20 mm being the preferred root diameter at the trailing end 26 when used singly, and 10–12 mm when used in pairs; a thread radius $R_1$ in the range of approximately 4–12 mm, with 9–10 mm being the preferred radius $R_1$ when inserted singularly and 5–7 mm when inserted side by side in pairs.

Referring to FIG. 3, a cross sectional view along line 3—3 of the implant 120 is shown. The implant 120 has an outer wall 144 surrounding an internal chamber 146. The large and small openings 140 and 142 may pass through the outer wall 144 to communicate with the internal chamber 146. The internal chamber 146 may be filled with bone material or any natural or artificial bone growth material or fusion promoting material such that bone growth occurs from the vertebrae through the openings 140 and 142 to the material within internal chamber 146. While the openings 140 and 142 have been shown in the drawings as being circular, it is appreciated that the openings 140 and 142 may have any shape, size configuration or distribution, suitable for use in a spinal fusion implant without departing from the scope of the present invention.

The implant 120 has a cap 148 with a thread 150 that threadably attaches to the insertion end 124 of the spinal fusion implant 120. The cap 148 is removable to provide access to the internal chamber 146, such that the internal chamber 146 can be filled and hold any natural or artificial osteoconductive, osteoinductive, osteogenic, or other fusion enhancing material. Some examples of such materials are bone harvested from the patient, or bone growth inducing material such as, but not limited to, hydroxyapatite, hydroxyapatite tricalcium phosphate; or bone morphogenic protein. The cap 148 and/or the spinal fusion implant 120 may be made of any material appropriate for human implantation including metals such as cobalt chrome, stainless steel, titanium, plastics, ceramics, composites and/or may be made of, and/or filled, and/or coated with a bone ingrowth inducing material such as, but not limited to, hydroxyapatite or hydroxyapatite tricalcium phosphate or any other osteoconductive, osteoinductive, osteogenic, or other fusion enhancing material. The cap 148 and the implant 120 may be partially or wholly bioabsorbable.

Referring to FIG. 3A, an alternative embodiment of implant 120 is shown and generally referred to by the numeral 120'. The implant 120' has a body 122' similar to body 122 of implant 120 and has an external thread 128' having a radius $R_3$ measured from the central longitudinal axis $L_3$ of the implant 120'. The thread radius $R_3$ is not constant throughout the length of the implant 120' and the external thread 128' has a thread height that is also not constant with respect to the body 122' of the implant 120'. In the preferred embodiment, the implant 120' has an external thread 128' with a radius $R_3$ that increases in size from the insertion end 124' to the trailing end 126' of the implant 120'.

Figure 4:
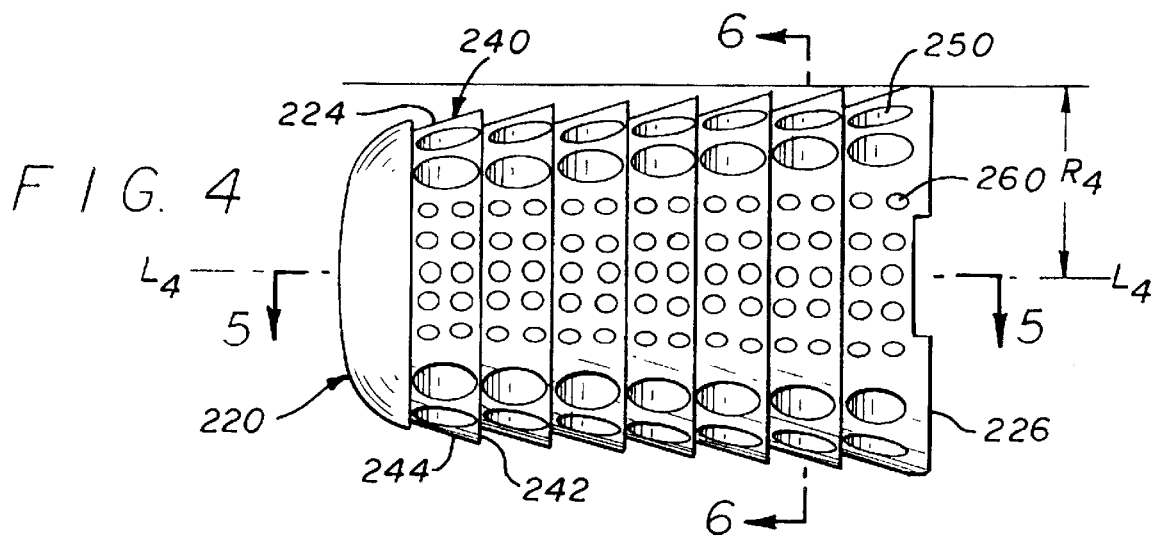
FIG. 4 is a side elevational view of an alternative embodiment of the spinal fusion implant having a frusto-conical body and a surface configuration comprising ratchetings for engaging bone, with wells and channels for bone ingrowth.

Referring to FIG. 4, an alternative embodiment of the spinal fusion implant of the present invention is shown and generally referred to by the numeral 220. The implant 220 has a frusto-conical body 222 and an outer locus that is generally frusto-conical substantially along the portion of the implant 220 that is in contact with the adjacent vertebrae of the spine. The implant 220 has a surface configuration of forward facing ratchetings 240 suitable for engaging the bone of the adjacent vertebrae. Each of the plurality of ratchetings 240 has a bone engaging edge 242 and ramped portion 244. The ratchetings 240 have a radius $R_4$ measured from the central longitudinal axis $L_4$ of the implant 220 that increases from the insertion end 224 to the trailing end 226. The height of the ratchetings 240 measured from the body 222 is constant throughout the length of implant 220.

The orientation of the ratchetings 240 makes the insertion of the implant 220 easier than its removal, as the ramped portions 244 act as an inclined plane on the way in, while the bone engaging edges 242 resist motion in the opposite directions. These forward facing ratchetings 240 tend to urge the implant 220 forward until the unremoved bone of the vertebrae blocks further motion resulting in a very stable spine and implant construct.

In the preferred embodiment, the bone engaging edges 242 of the ratchetings 240 have a height at a highest point measured from the body 222 (root diameter) of the implant 220 in the range of 0.25–2.0 mm, with the preferred height being 0.4 mm for use in the cervical spine and 1.25 mm for use in the lumbar spine.

Figure 5:
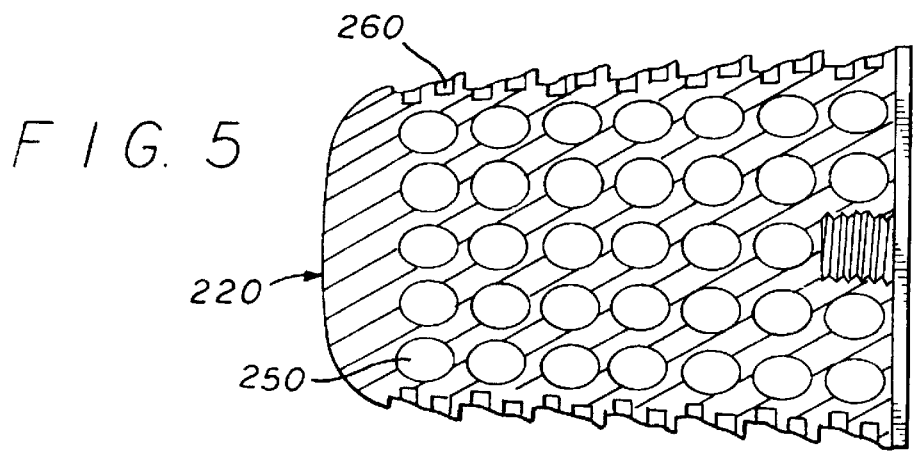
FIG. 5 is a cross sectional view along line 5—5 of the implant of FIG. 4 illustrating the channels and wells of the implant.
Figure 6:
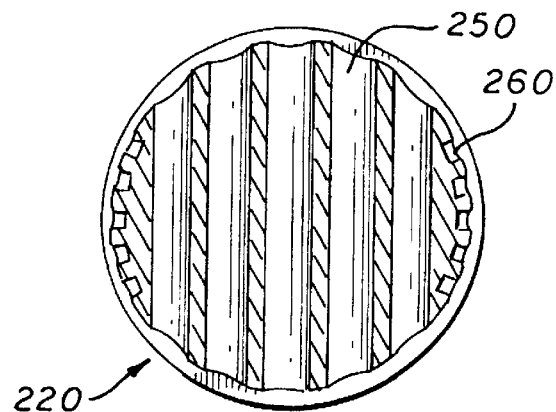
FIG. 6 is a cross sectional view along line 6—6 of the implant of FIG. 4 illustrating the channels and wells of the implant.

Referring to FIGS. 5 and 6, cross sectional views of implant 220 are shown. The implant 220 has channels 250 passing through the implant 220 and wells 260 formed in the surface of the implant 220. The wells 260 may or may not communicate with the channels 250. In the preferred embodiment of implant 220, the channels 250 have a diameter in the range of 0.1 mm to 6 mm, with 2–3 mm being the preferred diameter. The wells 260 have a diameter in the range of 0.1 mm to 6 mm, with 1–3 mm being the preferred diameter range. It is appreciated that although the channels 250 and wells 260 are shown having a generally rounded configuration, it is within the scope of the present invention that the channels 250 and wells 260 may have any size, shape, configuration, and distribution suitable for the intended purpose.

Figure 6A:
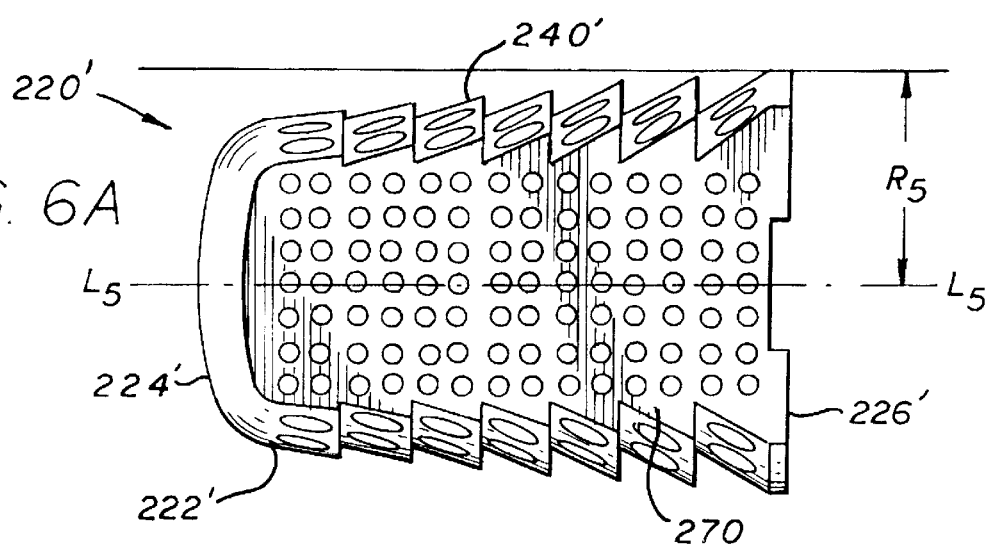
FIG. 6A is a side elevational view of an alternative embodiment of the spinal fusion implant having truncated sides forming a planar surface parallel to the longitudinal axis of the implant and ratchetings having a radius and height that are not constant.
Figure 6B:
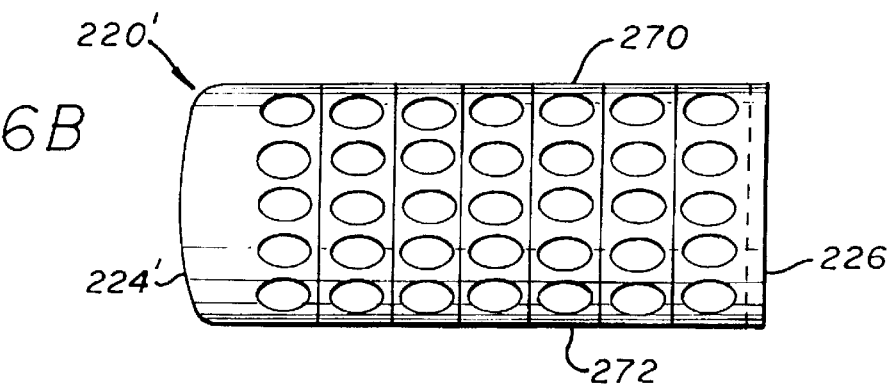
FIG. 6B is a top plan view of the spinal fusion implant shown in FIG. 6A.

Referring to FIGS. 6A and 6B, an alternative embodiment of the implant 220 is shown and generally referred to by the numeral 220'. The implant 220' is similar in configuration to implant 220 and has ratchetings 240' having a radius $R_5$ measured from the longitudinal central axis $L_5$ that increases in size from the insertion end 224' to the trailing end 226'. The ratchetings 240' each have a height measured from the body 222' that is not constant throughout the length of the implant 220'. In the preferred embodiment, the ratchet radius $R_5$ and the ratchet height increase in size from the insertion end 224' to the trailing end 226'.

As shown in FIG. 6B, the implant 220' has truncated sides 270 and 272 forming two planar surfaces which are diametrically opposite and are parallel to the longitudinal axis $L_4$. In this manner, two implants 2201 may be placed side by side with one of the sides 270 or 272 of each implant touching, such that the area of contact with the bone of the adjacent vertebrae and the ratchetings 240' is maximized. Alternatively, the implant 220' may have one truncated side.

Referring to FIG. 7, a side elevational view in partial cut-away of an alternative embodiment of the implant of the present invention is shown and generally referred to by the numeral 420. The implant 420 has a body 422 that is frusto-conical in shape substantially along the portion of the implant 420 that is in contact with the adjacent vertebrae of the spine and has an insertion end 424 and a trailing end 426. The implant 420 has an outer surface 438 that is capable of receiving and holding bone, or other materials capable of participating in the fusion process and/or capable of promoting bone ingrowth. In the preferred embodiment, the surface 438 comprises a plurality of posts 440 that are spaced apart to provide a plurality of interstices 442 which are partial wells with incomplete walls capable of holding and retaining milled bone material or any artificial bone ingrowth promoting material. The implant 420 may be prepared for implantation by grouting or otherwise coating the surface 438 with the appropriate fusion promoting substances.

Referring to FIG. 8, a side elevational view of an alternative embodiment of the spinal fusion implant of the present invention generally referred to by numeral 520 is shown. The implant 520 has a body 522 having a root diameter that is frusto-conical in the reverse direction as that of implant 20 shown in FIG. 1, in order to preserve and/or restore lordosis in a segment of spinal column when inserted from the posterior aspect of the spine. The body 522 has an insertion end 524 and a trailing end 526. In the preferred embodiment, the body 522 of the implant 520 has a minimum diameter at a point nearest to the trailing end 526 and a maximum diameter at a point nearest to the insertion end 524. The insertion end 524 may have an anterior nose cone portion 530 presenting a tapered end to facilitate insertion.

The implant 520 has an external thread 528 having a substantially uniform radius $R_6$ measured from the central longitudinal axis $L_6$ of the implant 520, such that the external diameter of the external thread 528 (major diameter) has an overall configuration that is substantially parallel to the longitudinal axis $L_6$. It is appreciated that the thread 528 can have a major diameter that varies with respect to the longitudinal axis $L_6$, such that the major diameter may increase from the insertion end 524 to the trailing end 526 or the reverse. The external thread 528 has a thread height measured from the body 522 that increases from the insertion end 524 to the trailing end 526.

Figure 9:
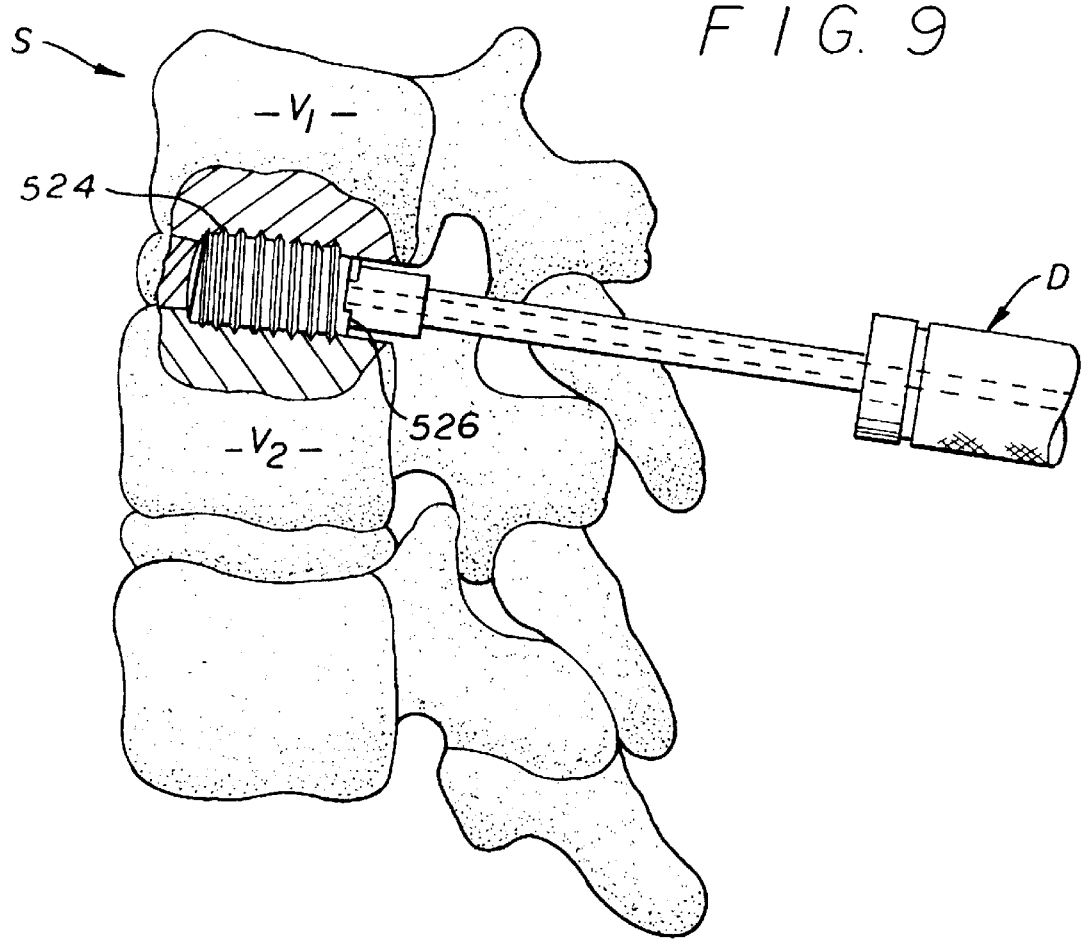
FIG. 9 is a side elevational view and partial cut-away of a segment of the spinal column in lordosis showing the spinal fusion implant of FIG. 8 being implanted with a driving instrument from the posterior approach to the spinal column.

Referring to FIG. 9, a segment of the spinal column S is shown with the vertebrae $V_1$ and $V_2$ in lordosis and an implant 520 shown being inserted from the posterior aspect of the spinal column S with an instrument driver D. The implant 520 is inserted with the larger diameter insertion end 524 first in order to in initially distract apart the vertebrae $V_1$ and $V_2$ which then angle toward each other posteriorly as the implant 520 is fully inserted. It is appreciated that the insertion of implant 520 does not require the adjacent vertebrae $V_1$ and $V_2$ to be placed in lordosis prior to insertion, as the full insertion of the implant 520 itself is capable of creating the desired lordotic angular relationship of the two vertebrae $V_1$ and $V_2$.

In the preferred embodiment of implant 520, for use in said lumbar spine, the implant 520 has an overall length in the range of approximately 24 mm to 30 mm, with 26 mm being the preferred length. The body 522 of the implant 520 has a root diameter at the insertion end 524 in the range of 12–22 mm, with 16 mm being the preferred root diameter at the insertion end, and a root diameter at the trailing end 526 in the range of 10–20 mm, with 14 mm being the preferred diameter at the trailing end 526. In the preferred embodiment, the implant 520 has a thread radius $R_6$ in the range of 6 mm to 12 mm, with 8 mm being the preferred radius $R_6$.

Referring to FIG. 10, an alternative embodiment of the spinal fusion implant of the present invention generally referred to by the numeral 620 and a partial fragmentary view of a second identical implant, generally referred to by the numeral 621 are shown. The implant 620 has a body 622 that is partially frusto-conical in shape similar to body 22 of implant 20 shown in FIG. 1, and has an insertion end 624 and a trailing end 626. The body 622 of the implant 620 has truncated sides 670 and 672 forming planar surfaces that are parallel to the longitudinal axis $L_7$. In this manner, two implants 620 and 621 may be placed side by side, with one of the sides 670 or 672 of each implant with little space between them, such that the area of contact with the bone of the adjacent vertebrae is maximized. It is appreciated that the body 622 may also be cylindrical in shape and have truncated sides 670 and 672.

The implant 620 has an external thread 628 having a radius $R_6$ measured from the central longitudinal axis $L_7$ that may be constant, such that the major diameter or outer locus of the external thread 628 has an overall configuration that is substantially cylindrical. It is appreciated that the external thread 628 may have a thread radius $R_7$ that is variable with respect to the longitudinal axis $L_7$ such that the major diameter or outer locus of the external thread 628 has an overall configuration that is substantially frusto-conical.

Figure 11:
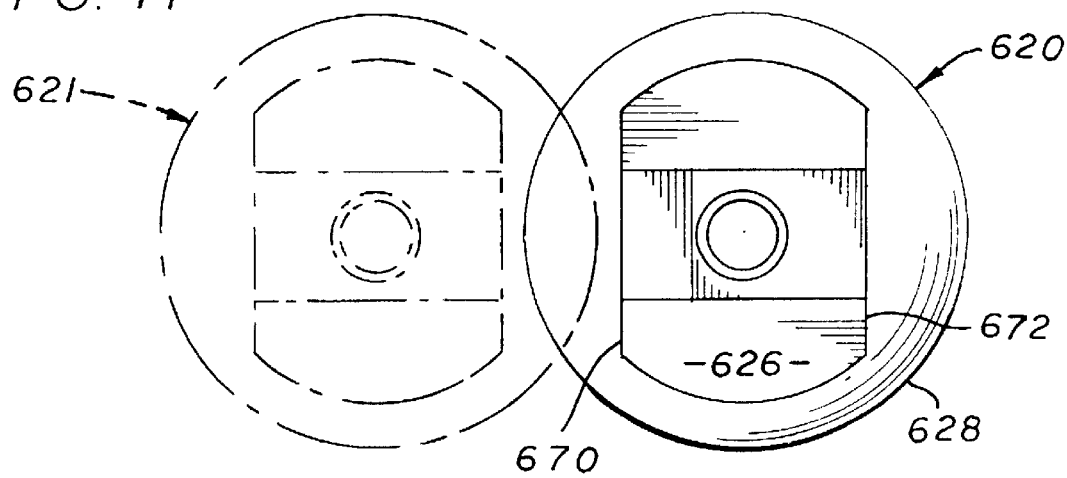
FIG. 11 is an end view along line 11—11 of the spinal fusion implant of FIG. 14 shown placed beside a second identical implant shown in hidden line.

Referring to FIG. 11, an end view of the implant 620 placed beside implant 621 is shown. The implant 620 has a thread radius that is substantially constant and has a thread height measured from the body 622 that is greater at the sides 670 and 672. In this manner, two implants 620 and 621 can be placed beside each other with the external thread 628 of each implant interdigitated allowing for closer adjacent placement of the two implants as a result of the substantial overlap of the external thread 628 at the side 670 or 672 of the implants.

Figure 12:
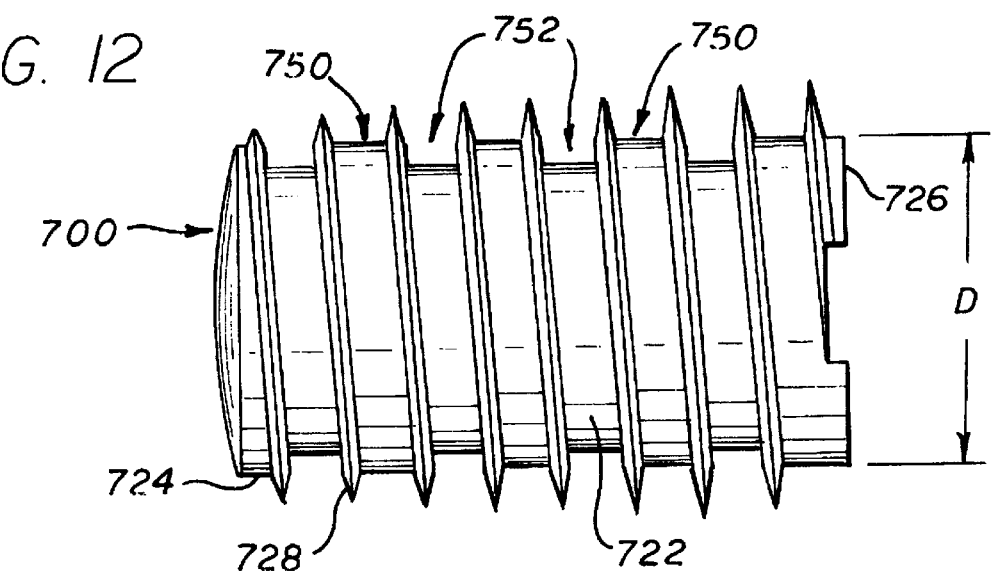
FIG. 12 is a side elevational view of an alternative embodiment of the spinal fusion implant having a body with an irregular configuration.

Referring to FIG. 12, an alternative embodiment of the implant of the present invention is shown and generally referred to by the numeral 700. The implant 700 is similar in configuration to implant 20 shown in FIG. 1, except that the body 722 has an irregular configuration. The configuration of the body 722 has a root diameter D which is variable in size throughout the length of the implant 700 and, as shown in this embodiment, comprises larger diameter portions 750 and smaller diameter portions 752. It is appreciated that each of the large diameter portions 750 may be of the same or different diameter and each of the smaller diameter portions 752 may be of the same or different diameter.

The outer surface of the body 722 of implant 720 may be filled with fusion promoting substances such that the smaller diameter portions 752 may hold such fusion promoting substances. If so filled, the composite of the implant 700 and the fusion promoting material could still produce an even external surface of the body 722 if so desired.

The Method Of The Present Invention

The embodiments of the frusto-conical implants of the present invention described above may be implanted with the method of the present invention described below.

In the preferred method of the present invention, the diseased disc between two vertebrae is at least partially removed from the anterior aspect of the spine. The two vertebrae adjacent the diseased disc are then optimally distracted and placed in the desired amount of lordosis by any of a number of well known means including, but not limited to, those means that distract the vertebral bodies by engaging screws placed into the anterior aspect of the vertebral bodies, and disc space distractors that are placed from the anterior aspect of the spine into the disc space and are then used to urge the vertebral endplates away from each other and into lordosis. When the correct amount of distraction and lordosis have been achieved at the affected disc level, then a frusto-conical space is created from anterior to posterior between the adjacent vertebrae. The frusto-conical space that is created is greater in diameter than the disc space height, such that some bone is removed from each of the adjacent vertebrae. The created space is generally frusto-conical in shape, being greatest in diameter anteriorly and tapering to a lesser diameter posteriorly.

It should be noted that where the spine is of sufficient width, it may be possible to prepare two such frusto-conical spaces side-by-side at the same disc level, allowing for the use of two implants instead of one. In either event, once the frusto-conical space is prepared and all debris removed, the implant is then inserted into the prepared space across the disc space, penetrating into each of the adjacent vertebrae, from anterior to posterior.

In the preferred embodiment, the diseased disc is first removed by conventional discectomy. The depth of the disc space is then determined by direct measurement. An interspace distractor such as that described by Michelson in U.S. patent application Ser. No. 08/396,414 entitled Apparatus and Method of Inserting Spinal Implants, incorporated herein by reference, is then inserted into the disc space. A series of such distractors are available and are sequentially inserted until the optimal amount of distraction across the disc space is achieved. The interspace distractors utilized for this purpose are wedged so as to induce physiological lordosis. An outer sleeve is then fitted over the barrel portion of the interspace distractor and firmly seated in engagement with the spine. As previously described in U.S. patent application Ser. No. 08/396,414, said outer sleeve may itself have extended portions capable of either maintaining or of obtaining and maintaining distraction. Said outer sleeve may also have vertebrae engaging prongs to further stabilize the outer sleeve to the spine and to more rigidly control motion at the adjacent vertebrae. As described in U.S. patent application Ser. No. 08/396,414, the use of the extended outer sleeve with distractor portions actually makes it possible to achieve the optimal distraction and lordosis without the use of the described interspace distractor. However, if the interspace distractor is used, then the outer sleeve is fully engaged to the spine, the distractor is removed, and in the preferred method by use of a slap-hammer, engaging the most proximal aspect of the distractor.

Figure 13:
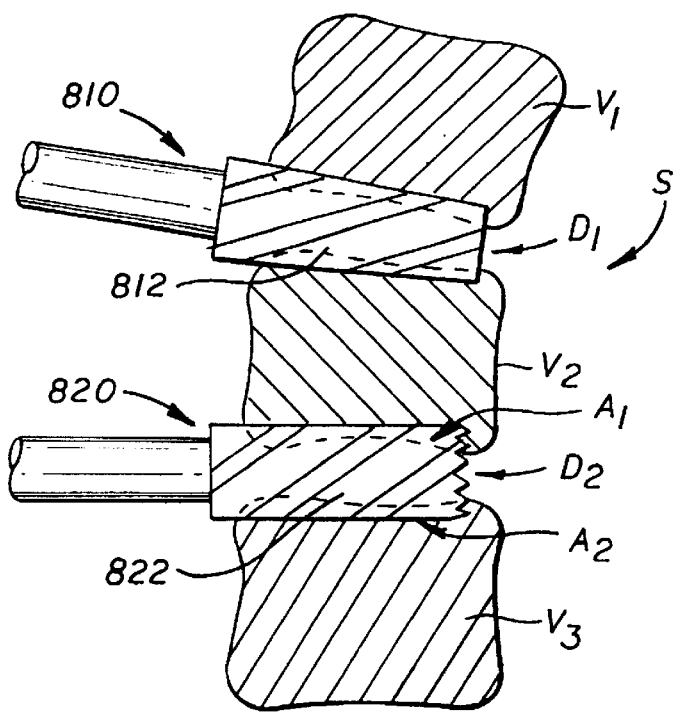
FIG. 13 is a side elevational view of a segment of the spinal column partially in lordosis showing a first drill and a second drill used in the method of the present invention.

Referring to FIG. 13, a segment of the spinal column S is shown with vertebrae $V_1$ and $V_2$ shown in lordosis adjacent to disc space $D_1$ and vertebrae $V_2$ and $V_3$ shown not in lordosis, but relatively parallel to each other adjacent disc space $D_2$. A first drill 810 making an opening 812 across the disc space $D_1$, and into adjacent vertebrae $V_1$ and $V_2$, and a second drill 820 making an opening 822 across the disc space $D_2$ and into adjacent vertebrae $V_2$ and $V_3$ are shown in FIG. 13. In the preferred embodiment, the interbody spinal fusion implant itself is threaded and frusto-conical in shape and therefore, the remaining portion of the procedure will be described in regard to that particular embodiment of the present invention, by way of example. With the disc space fully distracted and in anatomical lordosis and with the outer sleeve firmly engaged to the spine, it is then desirable to prepare the spine for receipt of the interbody fusion implant. It is preferable to prepare a space across the disc space and penetrating into the adjacent vertebrae which space corresponds roughly to the root dimensions of the implant to be implanted. For this purpose, a stopped-out bone cutting instrument is inserted through the outer sleeve, the shape of the cutting portion of the first drill 510 generally corresponding to the frusto-conical shape of the root diameter of the implant being inserted. This instrument may take the form of a frusto-conical drill or a mill and may be used to cut the bone by rotation, said rotation being achieved either through a manual handle or with power. Having prepared the space, the surgeon has two options. One is to remove the outer sleeve and then, because the implant is itself frusto-conical, screw the implant in using an implant driver capable of locking to the implant. The other is to leave the outer sleeve in place during the insertion of the implant.

If per the above, the surgeon wishes to remove the outer sleeve, the insertion of the implant itself causes a reproduction of the previous distraction which is easily achieved as the implant itself is frusto-conical in shape and the space created by the removal of the bone to either side of the disc space essentially corresponds to the root diameter of the implant such that as the implant is inserted, the threads are embedded into the vertebrae adjacent the disc space. Once the implant is fully inserted, the insertion apparatus is disconnected from the implant. If the cervical disc space is sufficiently wide from side-to-side, the procedure is performed in the same manner except that either a double-barrelled outer sleeve may be used or the previously described procedure essentially performed twice at the same disc level, such that a pair of implants may be inserted side-by-side.

In the alternative, if the surgeon wishes to leave the outer sleeve in place during the insertion of the implant and if the implant, as per this example has both a minor and a major diameter such as with a threaded implant, then the bone removing portion of the drilling means needs to generally correspond to the root diameter of the implant while the inside diameter of the outer sleeve needs to be great enough to allow the passage of the major diameter of the implant. It is desirable to stabilize the bone removal instrument and to assure that it removes equal portions of bone from each of the adjacent vertebrae. This may be achieved by a reduction sleeve which fits between the bone removal means and the inner wall of the outer sleeve and which essentially corresponds to the difference between the minor and major diameters of the implant, or some portion of the drill shaft proximal to the cutting end may have a diameter which corresponds to the major diameter of the implant even while the distal bone removing portion corresponds to the root diameter of the implant. In either way, the bone removal instrument is both stabilized and centered within the outer sleeve.

The approach to the lumbar spine may either be retroperitoneal, or transperitoneal. The procedure may be performed under direct vision, or laproscopically with the use of an endoscope. Generally it is preferable to utilize two implants which are inserted in an anterior to posterior direction, one to either side of the midline. The implants may be inserted using either a single-barrelled or double-barrelled outer sleeve, and by the methods previously described in the pending U.S. patent application Ser. No. 08/396,414 from which the present methods differ only in the shape of the drill end or bone milling device which is essentially conical. As also previously described, in copending application Ser. No. 08/396,414, the methods can be utilized for the insertion of non-threaded implants in which case said implants are linearly advanced rather than threaded in. And finally, as previously described in co-pending application Ser. No. 08/390,131, the implants themselves may have truncations on the sides to form a planar surface parallel to the longitudinal axis of the implant, such that it is possible to fit two such implants more closely together by narrowing the width of each while preserving their height.

As taught in copending application Ser. No. 08/396,414, a tap may be used after the drilling step and prior to the insertion of the implants.

Referring again to FIG. 13, in an alternative method of implant insertion, the use of at least partially frusto-conical interbody spinal fusion implants allows for the creation of lordosis by the implant itself where none is present to begin with as with the angular relationship of $V_2$ and $V_3$ shown in FIG. 13. As per this example, the disc space $D_2$ which in the preferred circumstance would be fully distracted but need not be, but lacking lordosis, could have a bore drilled across that space such that equal arcs of bone $A_1$ and $A_2$ are removed from each of the adjacent vertebrae $V_2$ and $V_3$ using a drill 820 or bone milling device capable of producing a cylindrical bore. Where one such boring is performed, it would generally be in the center line and directed from anterior to posterior. This might be appropriate for use in the cervical spine. More commonly and as generally would be the rule in the lumbar spine, a pair of bores would be so created from anterior to posterior, one to each side of the midline. The essential feature here is that the vertebrae $V_2$ and $V_3$, whether distracted from each other or not, are essentially lacking the full restoration of lordosis. The use of the substantially cylindrical bone drill 820 provides for the removal of a generally uniform thickness of bone from each of the adjacent vertebrae from anterior to posterior. The insertion of a frusto-conical implant, having a larger diameter at its trailing edge than at its leading edge, then forces the anterior aspects of the adjacent vertebrae apart more so than the posterior aspects where the diameter is lesser. This utilizes the implant to produce the desired lordosis.

The method for the insertion of the spinal fusion implants of the present invention from the posterior aspect of the spine is described in detail in co-pending patent application Ser. No. 08/396,414 and is incorporated herein by reference. Further, in the method of inserting the implants of the present invention from the posterior aspect of the spine, it is possible to place the adjacent vertebrae in lordosis prior to the bone removal step.

Figure 14:
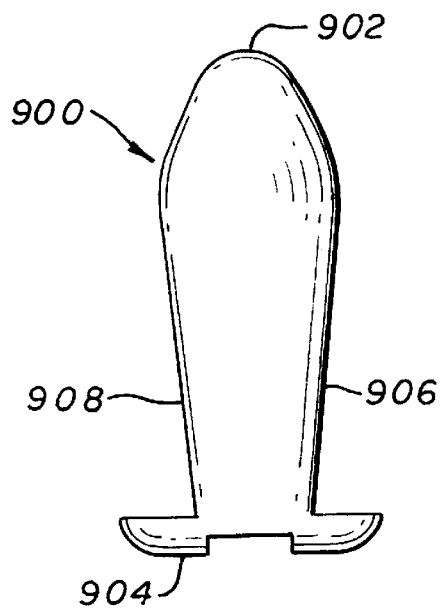
FIG. 14 is a side elevational view of the spinal distractor instrument of the present invention.
Figure 15:
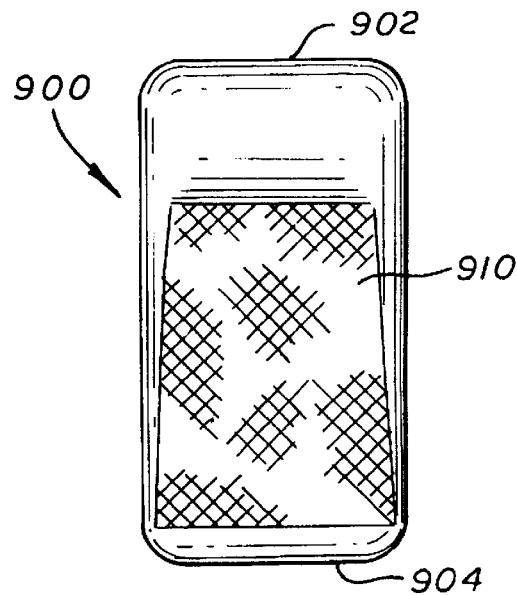
FIG. 15 is a top plan view of the spinal distractor instrument of FIG. 14.

Referring to FIGS. 14 and 15, spinal distractor 900 is shown which is used for distracting the adjacent vertebrae in lordosis prior to the bone removal step. The spinal distractor 900 has a tapered insertion end 902 to facilitate insertion, an instrument engaging end 904, and top and bottom surfaces 906 and 908. The top and bottom surfaces 906 and 908 are in a angular relationship to each other and are furthest apart at a point near the insertion end 902 to produce the desired lordosis when inserted in the disc space between two adjacent vertebrae. The top and bottom surfaces 906 and 908 have surface roughenings 910 for engaging the bone of the adjacent vertebrae and stabilizing the spinal distractor 900 when inserted.

When the human spine is viewed from the side, it consists of a balanced series of curves, as opposed to the vertebrae being stacked one upon another in a straight line when viewed from the side. In both the cervical and lumbar regions of the spine, the vertebrae relate to each other so as to form curves where the apex of said curves is displaced forward within the body, and those segments of the spine are said to be in lordosis. In contradistinction, in the thoracic portion of the spine, the vertebrae relate to each other so as to form a curve where the apex of said curve is displaced posteriorly and is said to be in kyphosis. The methods and instrumentation of the present invention have as one of its purposes to provide for the permanent stabilization of contiguous vertebrae by fusion, there is then a need for a means to preserve said lordosis/kyphosis if present, or to restore said lordosis/kyphosis if already lost, prior to the completion of the fusion procedure.

The following embodiments of the present invention, either individually or in combination, provide for both the stabilization and fusion to be performed with the related vertebrae in the correct anatomic lordosis or kyphosis. Where it is possible to approach the spine from various angles each of the devices, then has different forms appropriate to that specific approach.

Figure 16:
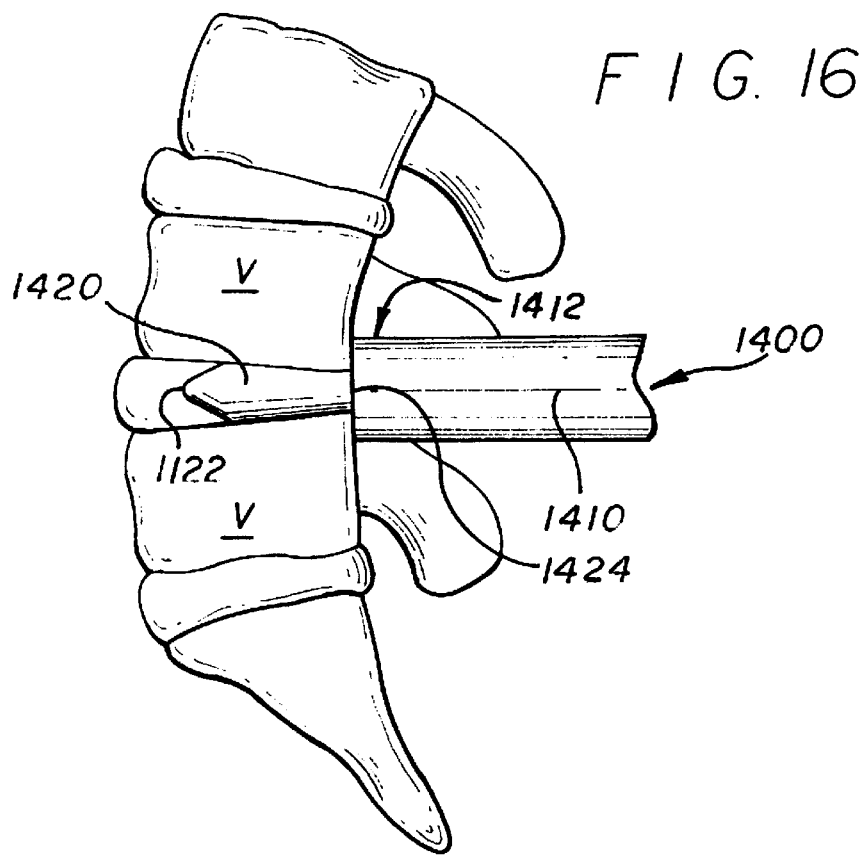
FIG. 16 is a side elevational view of a Posterior Long Lordotic Distractor inserted from the posterior aspect of the spine between adjacent vertebrae to restore and maintain lordosis of the spine.

Referring to FIG. 16, an alternative embodiment of the instrumentation of the present invention comprising a Posterior Long Lordotic Distractor 1400 capable of restoring and maintaining lordosis of adjacent vertebrae V from the posterior approach of the spine is shown. The Posterior Long Lordotic Distractor 1400 is inserted from the posterior aspect of the spine and comprises a barrel portion 1410 terminating at its distal end 1412 in a disc penetrating portion 1420 which is shown interposed within the disc space between two adjacent vertebrae V. The disc penetrating portion 1420 terminates distally into a leading bullet-shaped front end 1422 which facilitates the insertion of the disc penetrating portion 1420 between the adjacent vertebrae V. The disc penetrating portion 1420 is configured to have an uneven diameter such that it has a lesser diameter, and thus a lesser height within the disc space proximate the distal end 1412 of the barrel portion 1410 and has a greater diameter, and thus greater height within the disc space, in the direction of the front end 1422. This configuration of the disc penetrating portion 1420 serves to not only restore the intervertebral disc space height upon insertion of the disc penetrating portion 1420 of the Posterior Long Lordotic Distractor 1400, but also serves to restore and maintain the normal lordosis between the adjacent vertebrae V. The leading bullet-shaped front end 1422 is of particular importance in regard to the Posterior Long Lordotic Distractor 1400 where the largest diameter portion of the disc penetrating portion 1420 would otherwise be entering the disc space first.

The widest diameter of the disc penetrating portion 1420 is less than the diameter of the barrel portion 1410, such that a circumferential shoulder 1424 is formed at the distal end 1412 of the barrel portion 1410 which prevents over penetration into the disc space of the Posterior Long Lordotic Distractor 1400. It can readily be appreciated that such a configuration of the disc penetrating portion 1420 renders the Posterior Long Distractor 1400 quite stable within the disc space and resistant to backing out as the compressive forces of the spine upon the disc penetrating portion 1420 tend to urge it forward, while simultaneously the circumferential shoulder 1424 makes such further motion impossible, thus making the Posterior Long Distractor 1400 exceedingly stable.

Figure 17:
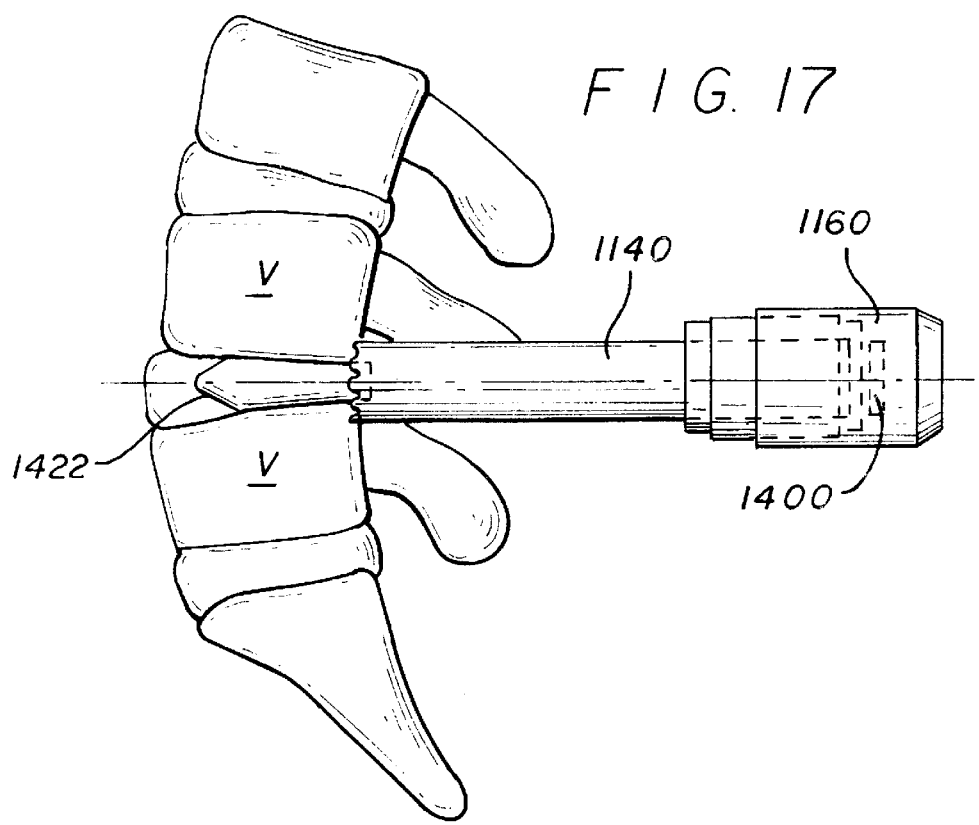
FIG. 17 is a side elevational view of the Posterior Long Lordotic Distractor shown partially in hidden line with the Outer Sleeve and Cap, inserted between adjacent vertebrae to restore and maintain lordosis of the spine with the Outer Sleeve engaging the vertebrae and properly seated over the Posterior Long Lordotic Distractor.

Referring to FIG. 17, in preparation for the bone removal step, the Posterior Long Lordotic Distractor 1400 is shown with the disc penetrating portion 1420 in place between the adjacent vertebrae V to restore and maintain lordosis of the spine. An Outer Sleeve 1140 described in reference to FIG. 5 of U.S. Pat. No. 5,484,437, is properly seated over the Posterior Long Lordotic Distractor 1400 using a mallet and the Driver Cap 160. While the bone removal step may be performed by either the drilling method described in reference to FIGS. 11A and 11C or the "Trephine Method" described in reference to FIG. 11B of U.S. Pat. No. 5,848,437, the "Trephine Method" is preferred in this situation as it leaves the Posterior Long Lordotic Distractor 1400 undisturbed until sufficient space has been created by the removal of bone at least as great as the thickness of the wall of the trephine 1270 itself to allow for the unobstructed removal of the Posterior Long Lordotic Distractor 1400.

If the "Trephine Method" described above in reference to FIG. 11B of U.S. Pat. No. 5,484,437 is used with the Posterior Long Lordotic Distractor 1400 the Outer Sleeve 1140 would first be fitted with an Inner Sleeve 1242 such as that shown in FIG. 11B, prior to both being placed simultaneously down over the barrel portion 1410 of the Posterior Long Lordotic Distractor 1400. Once the Outer Sleeve 1140 is concentrically seated relative to the barrel portion 1410, the Inner Sleeve 1242 alone would be removed, and the trephine 1270 would then be placed over the Posterior Long Lordotic Distractor 1400 and within the confines of the Outer Sleeve 1140 and into the adjacent vertebrae V across the disc space to the appropriate depth. The use of an Inner Sleeve is not required as the trephine 1270 is both centered and aligned by the Posterior Long Lordotic Distractor 1400.

In addition to cutting the two hemi-cylinders of bone, one for each vertebrae V, the saw-like sharp cutting teeth 1271 of the trephine 1270 shown in FIG. 11B removes a path of bone equal to the distance of the splaying out of each of the cutting teeth 1271 relative to its neighbor and which distance cannot be less than the wall thickness of the trephine 1270 itself. Thus, once the trephine 1270 is removed, left behind is a semi-cylindrical space outlining each of the arcs of bone cut from the adjacent vertebrae V such that the two spaces combined provide for sufficient space such that it is then possible to extract the Posterior Long Lordotic Distractor 1400 without disturbing the vertebrae V themselves as the vertebrae V are held in position by the Outer Sleeve 1140 which engages both of the vertebrae V.

Figure 18:
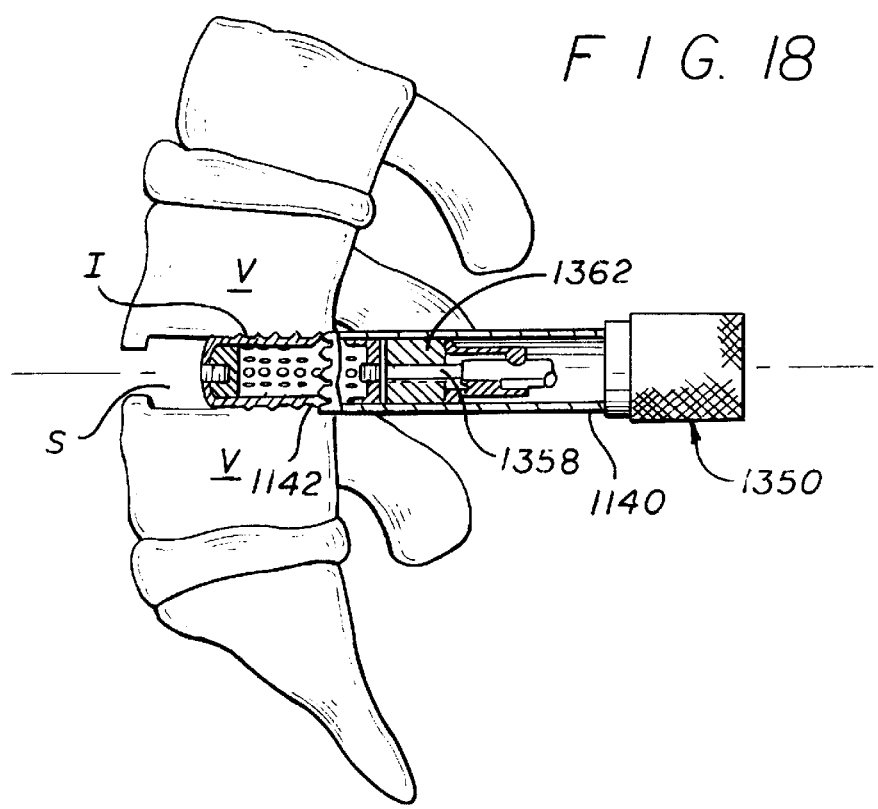
FIG. 18 is a side elevational view partially in cross section of a spinal implant being inserted through an Outer Sleeve between two adjacent vertebrae of the spine in which lordosis has been restored and maintained and in which a portion of bone has been removed from each vertebrae for receiving the spinal fusion implant.

Referring to FIGS. 18 and 19, since the vertebrae V are placed into lordosis prior to the bone removal step, the space S created by the bone removal is cut at an angle relative to the vertebrae V in the shape of a cylinder, and which corresponds to the shape of the cylindrical implant I. In this manner, the cylindrical implant I with parallel walls may be inserted between adjacent vertebrae V which have been stabilized for fusion in angular relationship to each other so as to preserve the normal curvature of the spine.

Referring to FIGS. 20 and 21, an elevational side view and a top plan view, respectively, of a Posterior Short Lordotic Distractor 1500 for posterior use generally referred to by the numeral 1500 is shown. The Posterior Short Lordotic Distractor 1500 is similar to the Short Distractor 1120 described in reference to the Convertible Distractor and comprises a disc penetrating portion 1520 identical to that of the Posterior Long Lordotic Distractor 1400 and an increased diameter head 128 as described in reference to FIGS. 3–3F of U.S. Pat. No. 5,484,437. As discussed above for the Posterior Long Distractor 1400, the configuration of the disc penetrating portion 1520 renders the Posterior Short Lordotic Distractor 1500 quite stable. This is an especially important feature for the Posterior Short Lordotic Distractor 1500 because it is left under the delicate dural sac and nerves while work is being performed on the contralateral side of the spine. If the Posterior Short Lordotic Distractor 1500 were other than stable, injury to these structures might result. To further prevent unwanted backing out of the Posterior Short Lordotic Distractor 1500, the bone engaging surface 1530 may be knurled or otherwise roughened, or have forward facing ratchetings.

Figure 22:
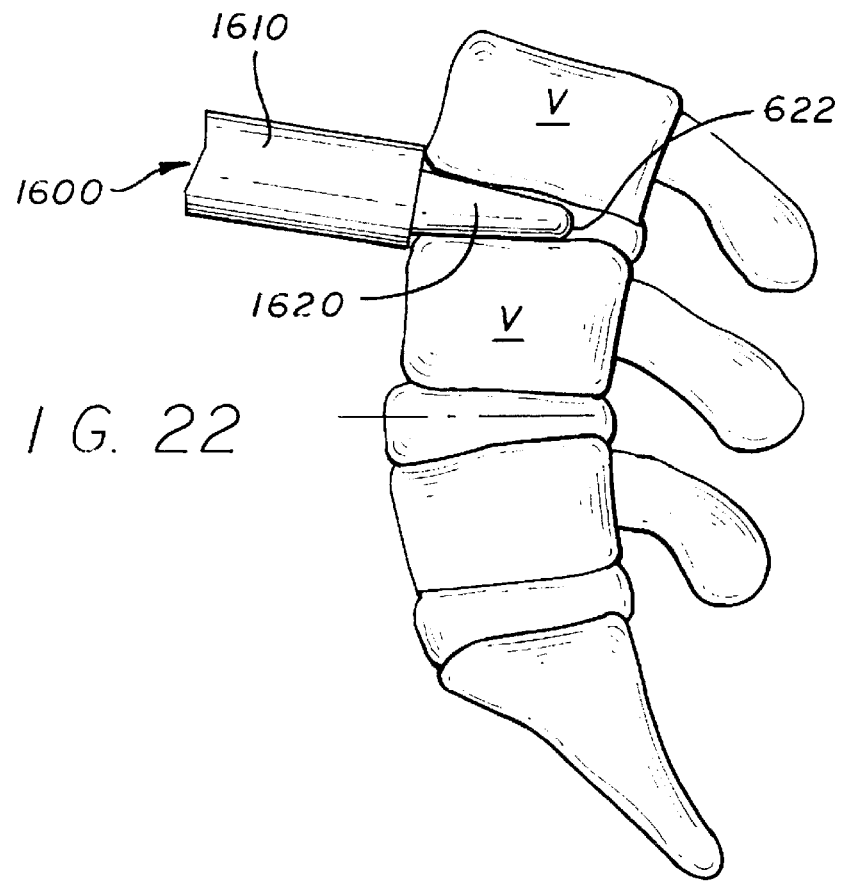
FIG. 22 is a side elevational view of an Anterior Long Lordotic Distractor of the present invention shown inserted between two adjacent vertebrae from the anterior aspect of the spine to restore and maintain lordosis.

Referring to FIG. 22, an Anterior Long Lordotic Distractor 1600 for use anteriorly within the spine is shown. It can be seen that the configuration of the disc penetrating portion 620 is the reverse of the disc penetrating portion 1420 of the Posterior Long Lordotic Distractor 1400 in that the disc penetrating portion 1620 is of greatest diameter and height proximate the barrel portion 1610 and that the diameter and height are diminished more distally in the direction towards the front end 1622 along the disc penetrating portion 1620. The Anterior Long Lordotic Distractor 1600 serves to restore and maintain lordosis of the spine by distraction of the adjacent vertebrae V. As described above for the Posterior Short Lordotic distractor 1500, it is appreciated that an Anterior Short Lordotic Distractor (not shown) having a disc penetrating portion 1520 may be similarly devised.

It can be seen that all of the lordotic distractors, both the anterior and the posterior embodiments, have specialized leading bullet-shaped or nosecone-shaped portions so as to facilitate the insertion of the disc penetrating portions within the disc space. This is of particular importance in regard to the Posterior Lordotic Distractors where the largest diameter portion of the disc penetrating portion 1420 would otherwise be entering the disc space first.

Figure 23:
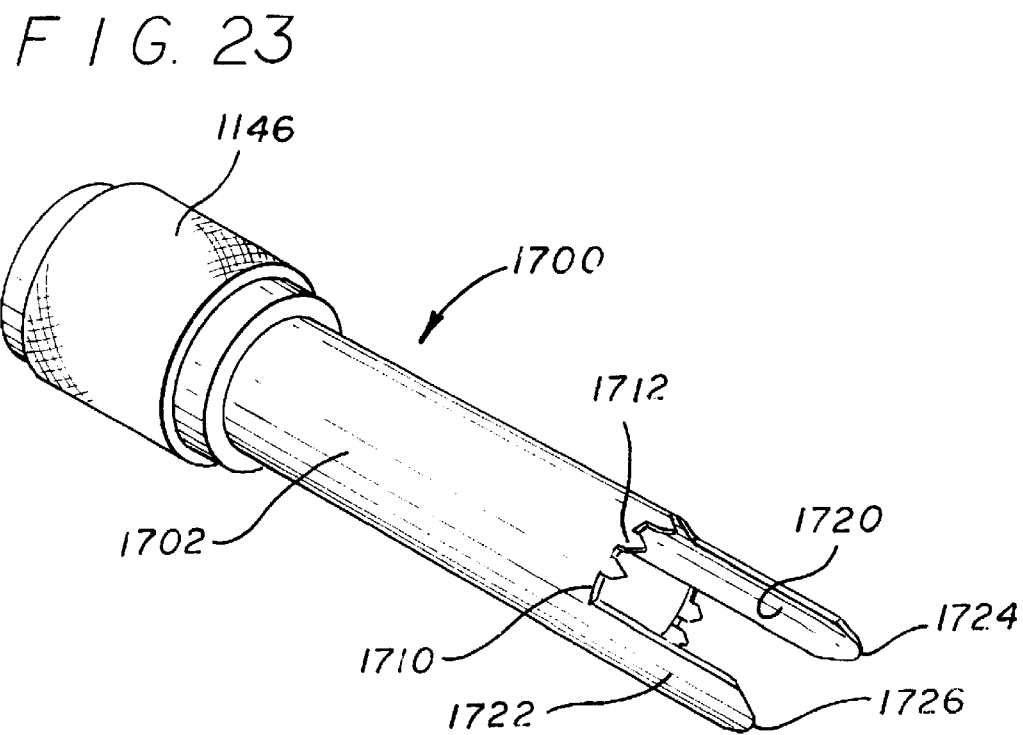
FIG. 23 is a perspective side view of the Extended Outer Sleeve of the present invention having extended members for insertion within the disc space and engaging means for engaging adjacent vertebrae of the spine.
Figure 24:
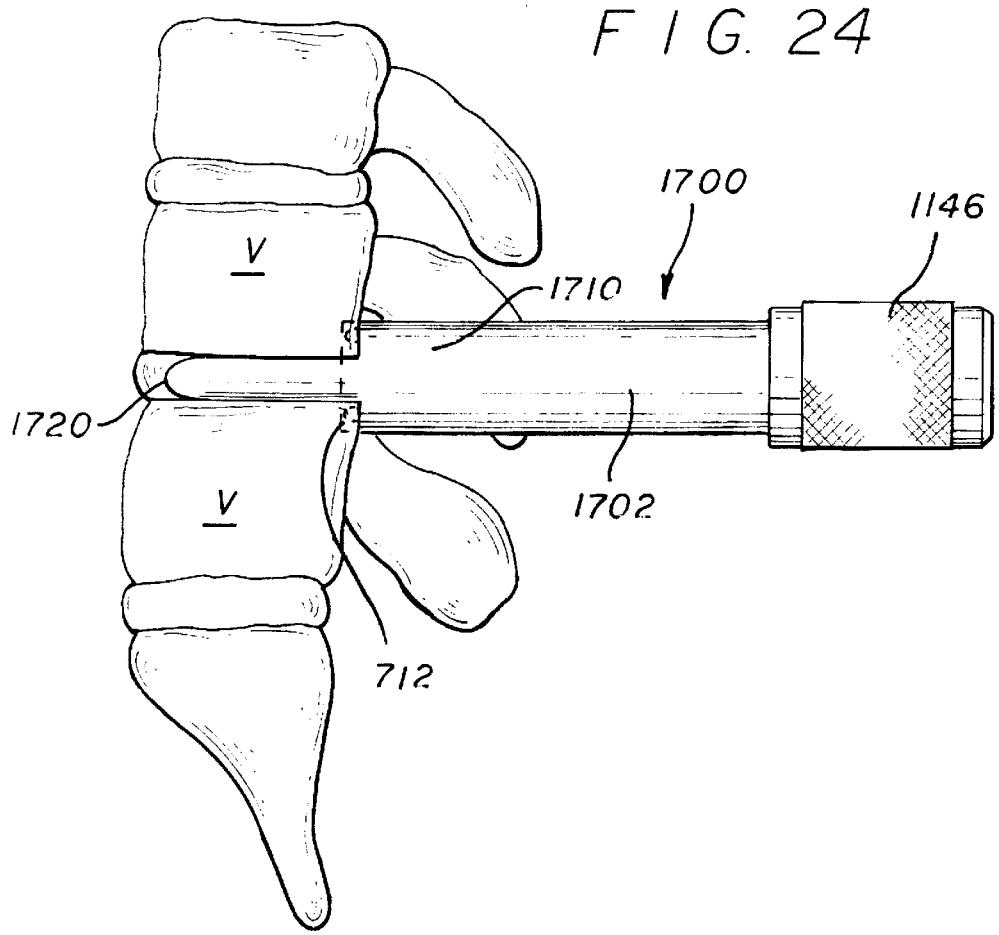
FIG. 24 is a side elevational view of the Extended Outer Sleeve of FIG. 23 shown inserted between adjacent vertebrae of the spine.
Figure 25:
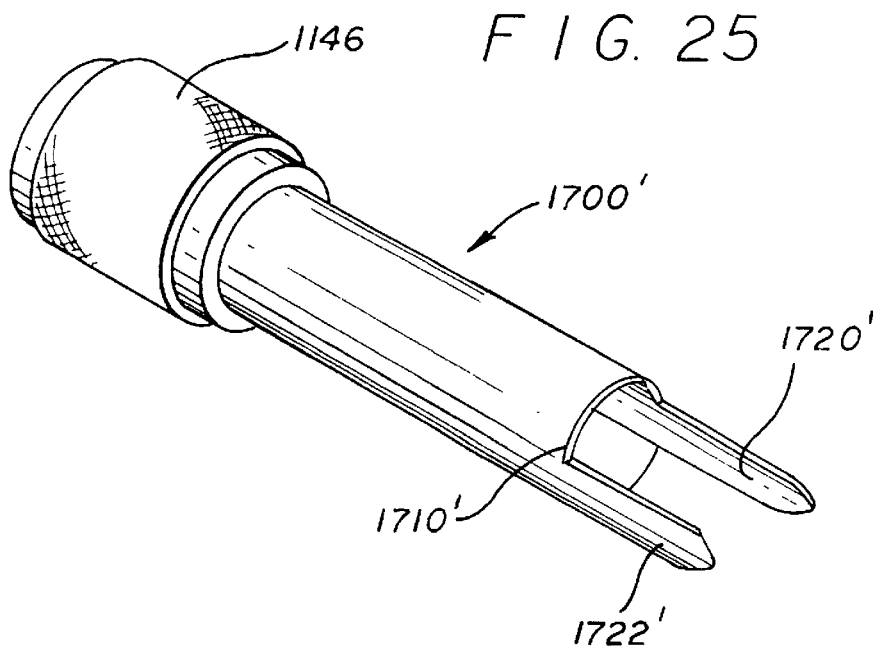
FIG. 25 is an alternative embodiment of the Extended Outer Sleeve of FIG. 23 shown without an engaging means for engaging adjacent vertebrae.

Referring to FIGS. 23 and 25, an alternative embodiment of the present invention for maintaining distraction during the surgical procedure involves a more specialized form of the previously described Outer Sleeve 1140 and is shown and identified as the Extended Outer Sleeve 1700. The Extended Outer Sleeve 1700 comprises a hollow tubular member 1702 having a distal end 1710 which has been extended such that a pair of extended portions 1720 and 1722, which are essentially a continuation of the hollow tubular member 1702 itself (with or without reinforcement), are opposed 180 degrees from each other, tapered at their leading edges 1724 and 1726 for ease of introduction, and of such height as to restore the height of the intervertebral disc space. Located at the distal end 1710 may be a plurality of teeth 1712, similar to those previously described above, or other engagement means for engaging the bone of the adjacent vertebrae V. It appreciated that the distal end 1710 may have no teeth 1712.

The Extended Outer Sleeve 1700 is entirely a new invention such as has never existed in the art or science of surgery, the Extended Outer Sleeve 1700 offers numerous advantages over all previously described drilling sleeves and the Outer Sleeve 1140 herein previously described. The Extended Outer Sleeve 1700 by dint of its extended portions 1720 and 1722 which are inserted between the adjacent vertebrae does itself act as an intervertebral distractor and is therefore essentially a combination outer sleeve and distractor. The Extended Outer Sleeve 1700 is exceedingly stable as the extended portions 1720 and 1722 are trapped within the disc space and further held there by the considerable compressive loads within the spine.

Referring to FIG. 25, because of the stability thus provided, a further derivative advantage is that the teeth 1772 on the distal end 1710 of the Extended Outer Sleeve 1700' may either be eliminated as shown in FIG. 26, or in the preferred embodiment be made of a lesser size. Further, it should be noted that teeth 1712 when present would be confined to the area directly in line with the vertebrae V and the extended portions 1720 and 1722 would ensure the proper rotatory alignment.

A further advantage, to be discussed in more detail subsequently, is that the extended portions 1720 and 1722 confine the surgery to the area within and between the extended portions 1720 and 1722 and protect all other tissues external to the extended portions 1720 and 1722.

Having now described the novel concept of the Extended Outer Sleeve 1700, attention may now be directed to further variations of the Extended Outer Sleeve 1700 capable of not only restoring and maintaining the appropriate intervertebral disc space height, but additionally being able to restore and maintain anatomic lordosis or kyphosis, as desired, throughout the surgical procedure.

Referring to FIG. 26, a Posterior Lordotic Extended Outer Sleeve 1800 for use from the posterior approach of the spine is shown. The Posterior Lordotic Extended Outer Sleeve 1800 comprises a hollow tubular member 1802 having a distal end 1810 which has been extended such that a pair of extended portions 1820 and 1822, which are essentially a continuation of the tubular member 1802, are opposed 1180 degrees from each other. The extended portions 1820 and 1822 differ from the extended portions 1720 and 1722 in that the extended portions 1820 and 1822 are configured to restore and maintain lordosis of the spine similar to the disc penetrating portion 1420 of the Posterior Long Lordotic Distractor 1400, the features of which are herein incorporated by reference.

The extended portions 1820 and 1822 each have a height that is lesser at a point proximate the distal end 1810 of the tubular member 1802 that increases in the direction away from the tubular member 1802. The extended portions 1820 and 1822 are tapered at their leading edges 1824 and 1826, respectively to facilitate insertion into the disc space.

Between the extended portions 1820 and 1822, may be a plurality of teeth 1812 for engaging the bone of the vertebrae V when the Extended Outer Sleeve 1800 is inserted within the disc space between the adjacent vertebrae V.

Referring to FIG. 27, a Posterior Lordotic Extended Outer Sleeve 800' in place within the intervertebral disc space is shown.

Referring to FIG. 28, an Anterior Extended Outer Sleeve 900 for use from the anterior approach of the spine is shown. The Anterior Lordotic Extended Outer Sleeve 1900 comprises a hollow tubular member 1902 having a distal end 1910 which has been extended such that a pair of extended portions 1920 and 1922 which are essentially a continuation of the tubular member 1902 and are opposed 1180 degrees from each other. The extended portions 1920 and 1922 differ from the extended portions 1820 and 1822 in that the extended portions 1920 and 1922 are configured to restore and maintain lordosis of the spine from the anterior approach similar to the disc penetrating portion 1620 of the Anterior Long Lordotic Distractor 1600, the features of which are herein incorporated by reference.

The extended portions 1920 and 1922 each have a height that is greater at a point proximate to the distal end 1910 of the tubular member 1902 that decreases in the direction away from the tubular member 1902. The extended portions 1920 and 1922 are tapered at their leading edges 1924 and 1926, respectively to facilitate insertion into the disc space.

While the Lordotic Extended Outer Sleeve for use anteriorly is shown in the singular form and in use in the lumbar spine, it is understood that it may take a double barrelled form and in either form, be used throughout the spine.

Figure 29:
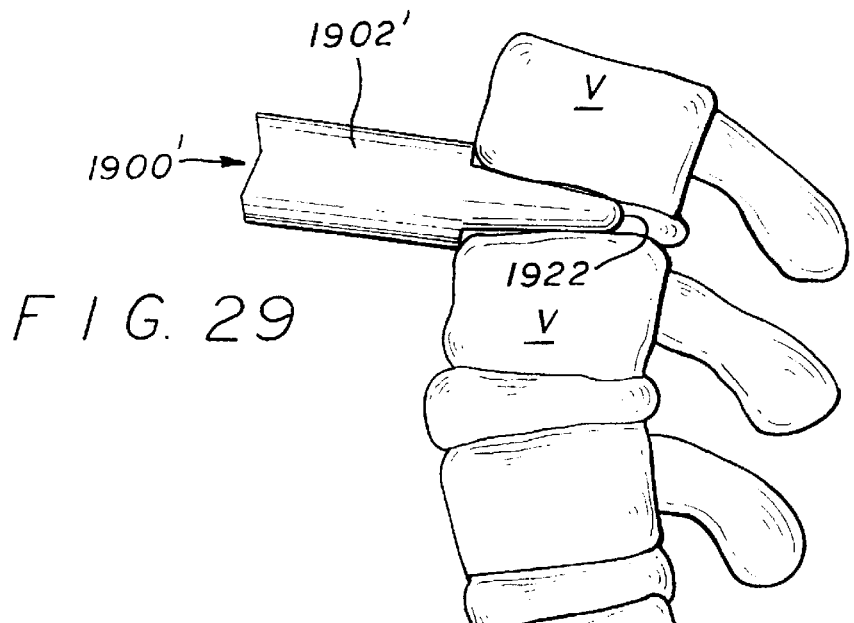
FIG. 29 is a side elevational side view of an alternative embodiment of the Anterior Lordotic Extended Outer Sleeve of FIG. 28 absent the engagement means for engaging the vertebrae, inserted between adjacent vertebrae from the anterior aspect of the spine.
Figure 30:
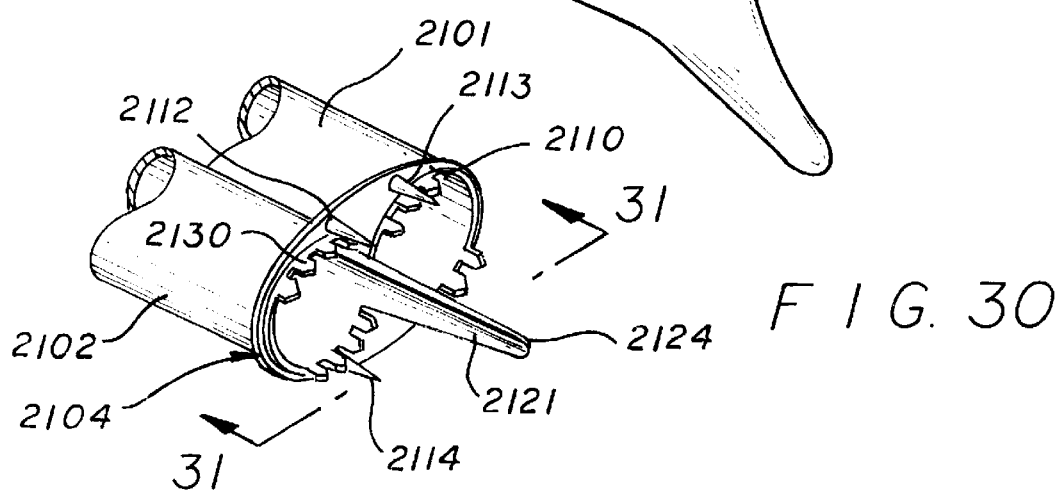
FIG. 30 is a perspective side view of a Dual Extended Outer Sleeve having an uneven extended portion which decreases in height in the direction of insertion.

Referring to FIGS. 29 and 30, a Lumbar Dual Extended Outer Sleeve is shown and generally referred to by the numeral 2100. The Dual Extended Outer Sleeve 2100 comprises two hollow tubular members 2101 and 2102. The two hollow tubular members 2101 and 2102 have a distal end 2104 which has been extended to form an extended portion 2121 which is essentially a continuation of the hollow tubular members 2101 and 2102 joined together. The extended portion 2121 is similar in shape and function to the extended portions 2920 and 2922 described above in reference to FIG. 31. The extended portion 2121 has a height that is greater at a point proximate the distal end 2104 and decreases in the direction away from the hollow tubular members 2101 and 2102, in order to maintain the normal curvature of th e spine by correcting the angular relationships of the vertebrae V. The extended portion 2121, is tapered at its leading edge 2124 to facilitate insertion of the extended portion 2121 into the disc space between two adjacent vertebrae V. Located at the distal end of the tubular members 2101 and 2102 are sharpened teeth 2130 for engaging the vertebrae V.

Each of the hollow tubular members 2101 and 2102 are displaced from each other ideally the sum of the difference between the minor and major diameters of two threaded spinal implants I combined, but not less than that difference for one implant I, as it is possible to have the threads of one implant I nest interposed to the threads of the other implant I such that they both occupy a common area between them. Typically, the walls of each hollow tubular members 2101 and 2102 have a combined thickness at the point which the walls of the hollow tubular members 2101 and 2102 are in contact with each other which is approximately 2.0 mm. This is achieved by machining away part of each hollow tubular member 2101 and 2102 to reduce the wall thickness of each hollow tubular member 1101 and 1102 prior to joining them together. In this manner, the two hollow tubular members 2101 and 2102 may be placed closer together so that two spinal implants I may be placed closer together when inserted within the disc space between adjacent vertebrae W. The hollow tubular member 2101 and 2102 can be overlapped or displaced from each other so as to control the distance between implants when the Dual Extended Outer Sleeve is utilized and two implants implanted.

The hollow tubular members 2101 and 2102 may be bridged in part or wholly throughout their length, but are typically fixed by a foot plate 2110, similar in function, but not in configuration, to Foot Plate 344 described above in reference to FIGS. 7C and 7D.

Figure 31:
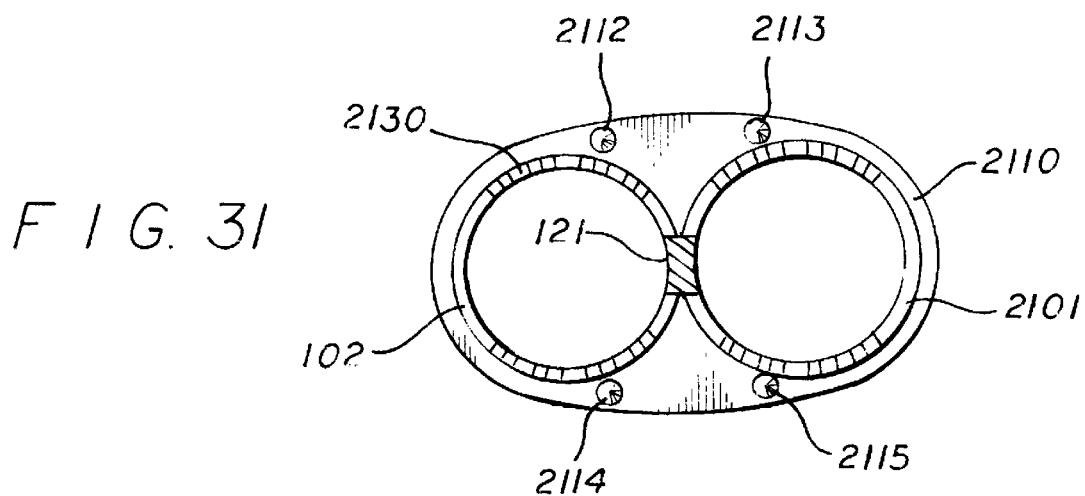
FIG. 31 is bottom plan view of the foot plate of the Dual Extended Outer Sleeve of FIG. 30.

Referring specifically to FIG. 31, the foot plate 2110 has an oval configuration that contours and hugs the vertebrae and has a plurality of prongs 2112–2115 extending from the bottom of the foot plate 2110 is shown. The prongs 2112–2115 are sufficiently long to engage the bone of adjacent vertebrae V, but limited in length so as not to over penetrate beyond the vertebrae once inserted.

Figure 32:
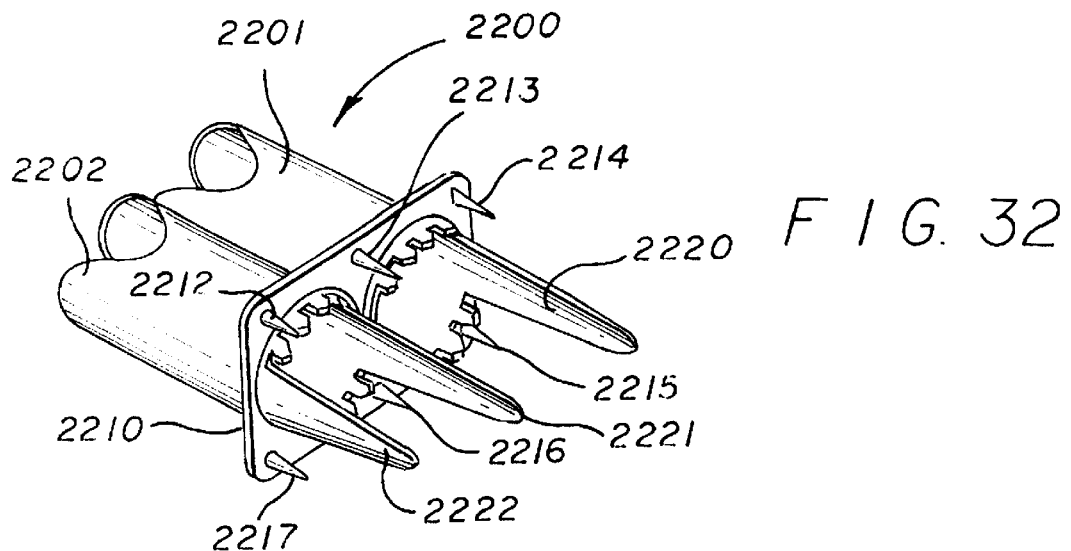
FIG. 32 is a perspective side view of a Dual Extended Outer Sleeve having uneven extended portions which decrease in height in the direction insertion.

Referring to FIG. 32, a second Dual Extended Outer Sleeve 2200, is shown. The Dual Extended Outer Sleeve 1200 is similar to the Dual Extended Outer Sleeve 2100, except that it has additional extended portions 2220 and 2222 which have a height that is greater near the distal end 2204 of the hollow tubular members 2201 and 2202 and decreases in the direction away from the hollow tubular members 2201 and 2202. The extended portions 2220–2222 are similar in shape and function to the extended portions 2920 and 2922 described above in reference to FIG. 31. Moreover, as the foot plate 2210 is rectangular and larger than foot plate 2110, additional prong 2216 and 2217 may be added.

Further, it should be appreciated that the lordotic distractor for use posteriorly when referring to their use in the lumbar spine, would be used anteriorly if applied to the thoracic spine, either in the single or double-barrel form. This is because the thoracic spine is normally curved into kyphosis which is the reverse of lordosis. That is, in approaching the thoracic spine anteriorly, it would be desirable to distract the back of the disc space more than the front, and that would require an Extended Outer Sleeve which would resemble that seen in FIG. 28; though when used in this new context, it would more correctly be referred to as an Anterior Thoracic Kyphotic Extended Outer Sleeve. As with the Posterior Lordotic Outer Sleeve, the Posterior and Anterior Long Lordotic Posterior Short Lordotic Distractor and Anterior Short Lordotic Distractors, though referred to previously as lordotic when placed into the lumbar spine from the posterior approach, would now more correctly, when placed in the thoracic spine from the anterior approach be called Kyphotic Thoracic Distractors.

It can readily be appreciated that the described Extended Outer Sleeves may be used with the Short and Long Distractors having a disc penetrating portion of uniform diameter or in combination with the lordotic and kyphotic distractors of complimentary configuration.

Referring to FIGS. 33–38, shown is the apparatus 2350 for use in installing an improved interbody spinal fusion implant 2300 having one or more flat sides as disclosed in co-pending application filed on Feb. 17, 1995, entitled IMPROVED INTERBODY SPINAL FUSION IMPLANTS which is incorporated herein by reference. The apparatus 2350 comprises a Dual Outer Sleeve 2310 having a pair of overlapping, hollow cylindrical tubes 2352 and 2354 identical in size and each having an internal diameter slightly larger than the outer diameter of the spinal fusion implant. The cylindrical tubes 2352, 2354 are in communication with each other along their length and are displaced from each other ideally a distance that is slightly greater than the sum of the diameters of two spinal fusion implants 2300 placed side-by-side with the flat sides of each spinal fusion implant touching. The cylindrical tubes 2352 and 2354 are joined longitudinally such that they are partially overlapping. The hollow cylindrical tubes 2352 and 2354 are mounted on a foot plate 2362 similar to the foot plate described in FIG. 32. There are a series of prongs 2364a–2364f projecting from the bottom 2366 of the foot plate 2360 which are used to engage the Dual Outer Sleeve 2310 to the base of the adjacent vertebrae V.

Figure 34:
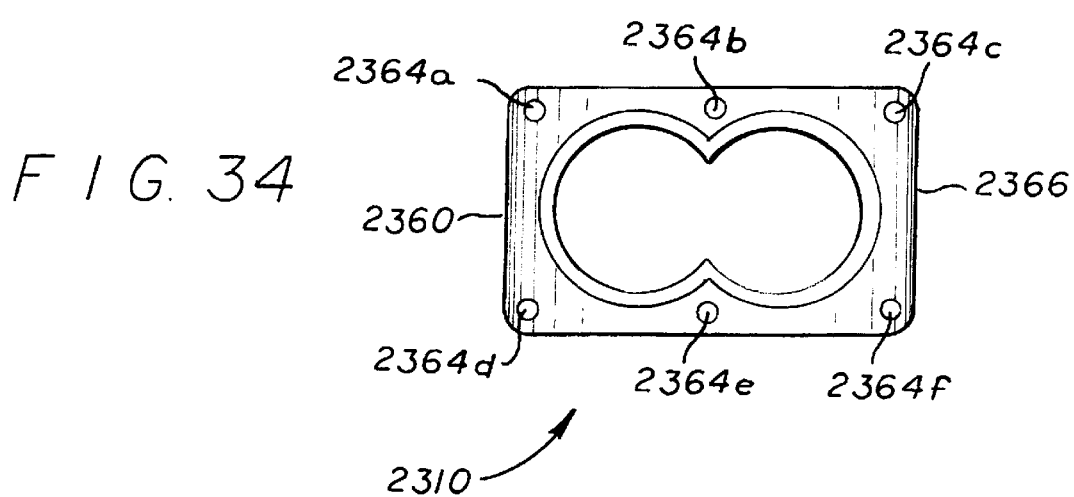
FIG. 34 is a bottom plan view of the foot plate of the apparatus of the present invention for use in installing the interbody spinal implants having one or more flat sides.

Referring specifically to FIG. 34, the apparatus 2350 is introduced over two Long Distractors 2320 and 2322 placed side-by-side and protruding anteriorly from the vertebrae V. The Long Distractors 2320 and 2322 are similar to the Long Distractor 100 described in U.S. Pat. No. 5,484,437 except that they have a flat side 2324 and 2326, respectively.

Figure 35:
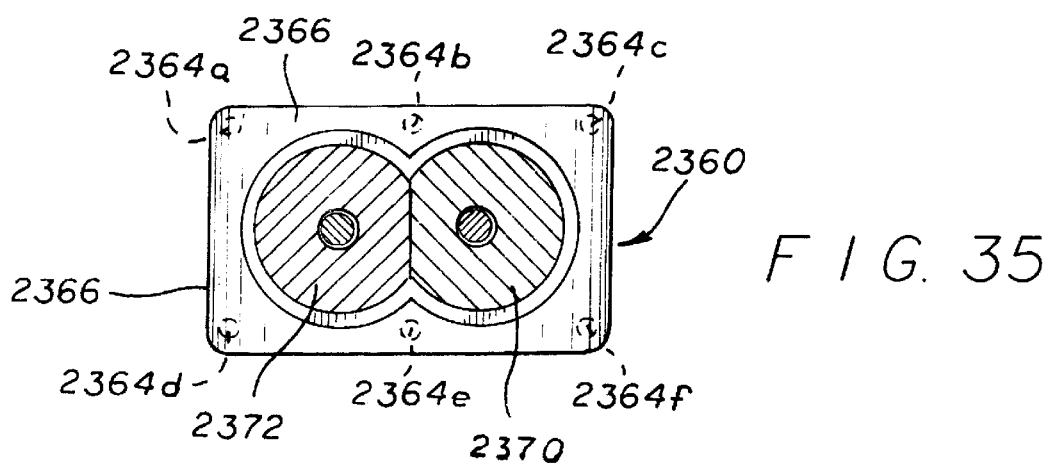
FIG. 35 is a cross sectional view along line 35—35 of FIG. 33 illustrating the apparatus used for inserting interbody spinal implants having one or more flat sides.

Referring to FIGS. 34 and 35, in one embodiment, the foot plate 2360 is essentially rectangular, but without sharp corners. It is appreciated by those skilled in the art, that other shapes can be utilized.

Figure 33:
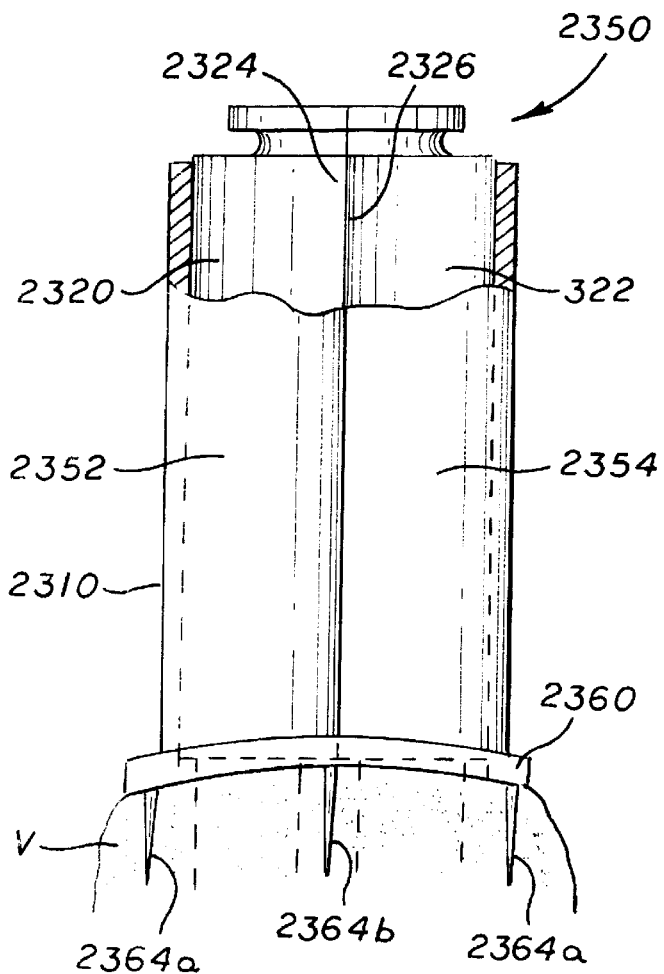
FIG. 33 is an elevational front view of the apparatus of the present invention for use in installing interbody spinal implants having one or more flat sides, shown placed over two Long Distractors with the prongs inserted into the vertebrae.
Figure 36:
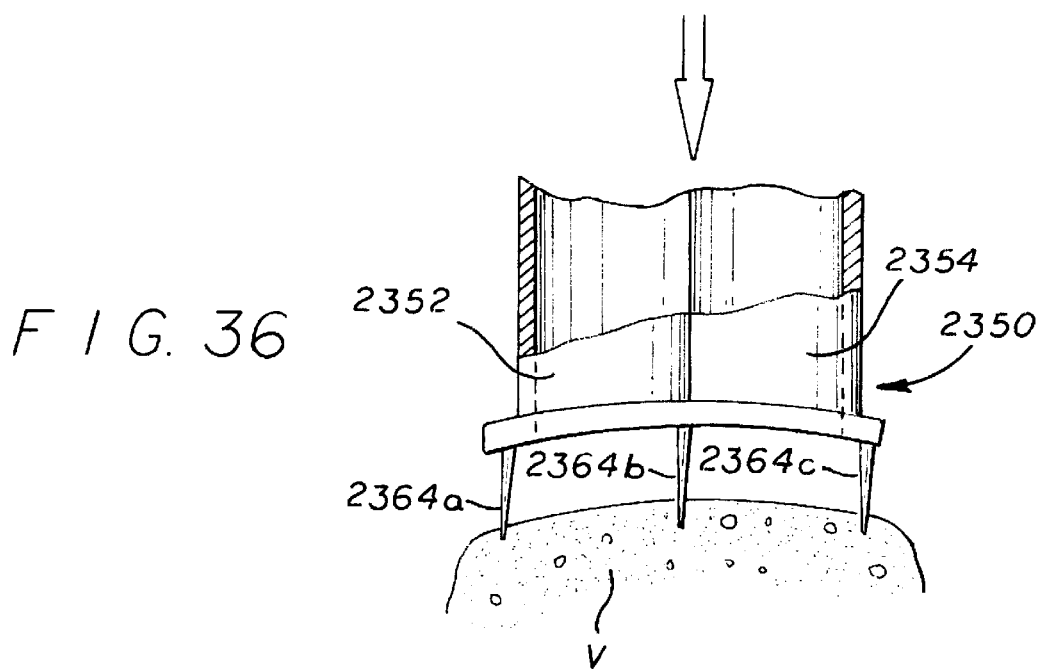
FIG. 36 is a partial fragmentary view of the apparatus of the present invention for use in installing interbody spinal implants having one or more flat sides, shown with the prongs being partially inserted into the vertebrae.

As shown in FIGS. 33 and 36, the foot plate 1360 is contoured so as to approximate the external curvature of the vertebrae V anteriorly. Extending forward from foot plate 1360 are the multiple sharp prongs 2364a–2364f which are sufficiently long to permit fixation of the foot plate 2360 to the vertebrae V. The prongs 2364a–2364f are limited in length so as to not penetrate the vertebrae V too far posteriorly and number from 2 to 10, but preferably 6.

Referring to FIG. 36, as the Dual Outer Sleeve 2350 is driven forward, the prongs 2364a–2364f extending from foot plate 2360 are embedded into the opposed vertebrae V until their forward motion is inhibited by the foot plate 2360 becoming congruent to and being stopped by, the anterior aspect of the vertebrae V.

As shown in FIG. 33, once the apparatus 2350 has been fully seated, the vertebrae V adjacent the interspace D to be fused are rigidly held via foot plate 2360 and the prongs 2364a–2364f. Thus, it is possible to remove either one, or if desired, both of the long distractors 2320 and 2322. The dual outer sleeve has been described above for inserting two implants each having at least one flat side, may have extended portions for intradiscal insertion which are capable of producing distraction as well as kyphosis or lordosis as previously described with such extensions extending in line with the lateral walls of the cylindrical tubes.

Figure 37:
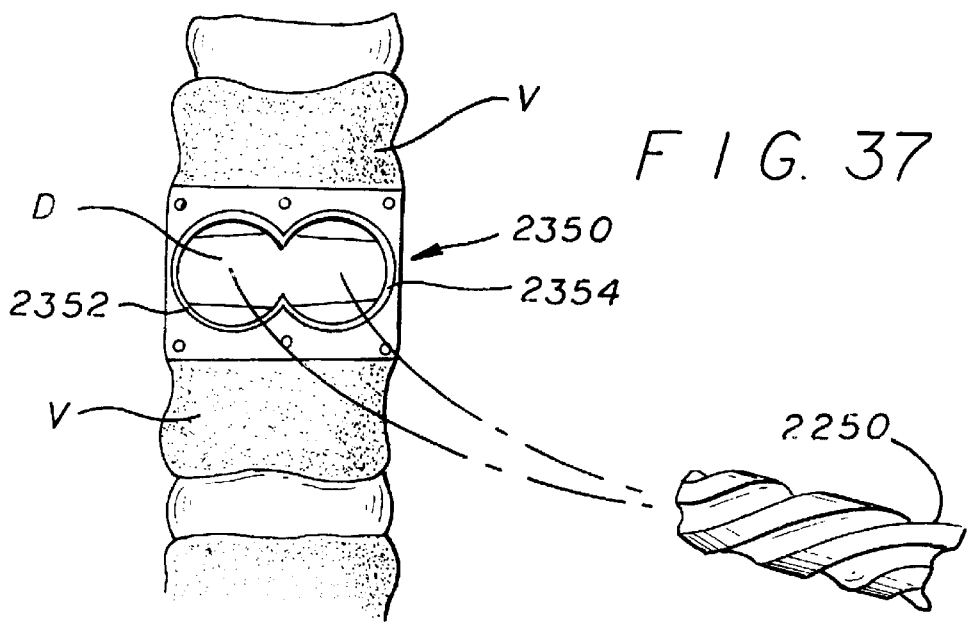
FIG. 37 illustrates a step of the method of drilling a hole into a vertebrae with the apparatus of the present invention for use in installing interbody spinal implants having one or more flat sides, shown engaged to two adjacent vertebrae of a spinal column.

Referring to FIG. 37, once the Dual Outer Sleeve 2350 has been fully seated, one of the Long Distractors 2320 and 2322 is removed and the surgeon may drill the interspace D utilizing drill 250 using each of the hollow cylinders 2352, 2354 to guide the drill 250 in order to create overlapping holes in which the spinal fusion implants 2300a and 2300b may be inserted. It is also appreciated by those skilled in the art, that a hollow inner sleeve (not shown) may be inserted into the hollow cylinders 2352, 2354 through which the drilling is performed or the Long Distractors may be left in place and a hollow trephine that fits over each of the Long Distractors 2320 and 2322 may be used to drill the interspace D. It is readily appreciated that the tubular members can be of a variety of shapes and sizes. Further, the removal of disc and bone may be accomplished by the use of a burr, or a chisel of appropriate shape for that purpose and with or without the use of a drill. The implants would then have shapes appropriate for use in the spaces so formed.

Figure 38:
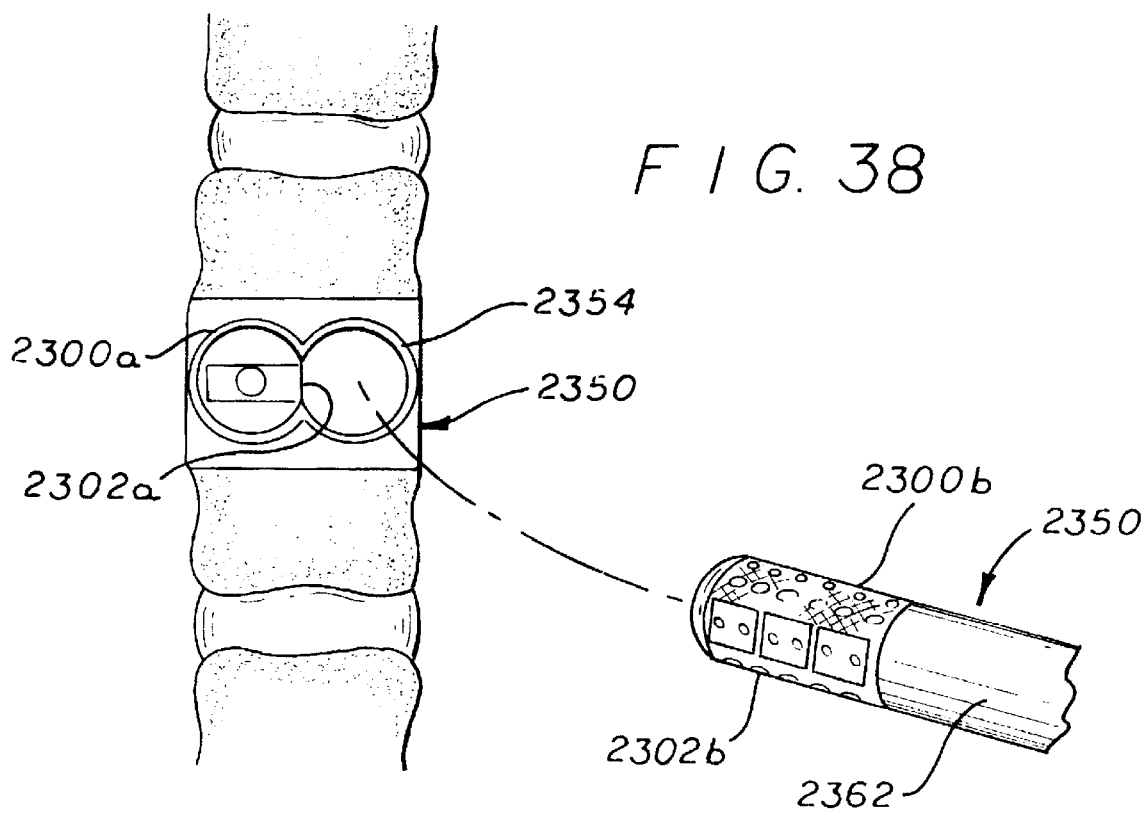
FIG. 38 illustrates a step of the method of the present invention for inserting a second interbody spinal implant having one or more flat sides into the interspace between two adjacent vertebrae with one implant shown already installed in place.

Referring to FIG. 38, once the interspace D has been drilled, an implant Driver 350 described above is used to insert the spinal fusion implants 2300 and 2300b preferably by linear advancement. The implant driver instrument 350 may be used to either insert or to remove the spinal fusion implants 2300a and 2300b.

Once affixed to the implant Driver 350, the spinal fusion implant 2300a is then introduced through one of the hollow cylindrical tubes 2352,2354 and driven into the interspace D by the application of an impaction force transmitted through the implant driver instrument 350. Once the spinal fusion implant 2300a is inserted into the interspace D, the surface roughenings of the outer surface of the spinal fusion implant 2300a engage the bone of the vertebrae V and the implant Driver 350 is detached from the spinal fusion implant 2300a. The implant driver instrument 350 is then withdrawn from the Dual Outer Sleeve 2350 and the spinal fusion implant 2300a is fully installed and inset in the interspace D as shown in FIG. 38.

Once a first spinal fusion implant 2300a is inserted into the interspace D, a second spinal fusion implant 2300b is driven into the interspace D so that the flat side 2302a or 2302b of each spinal fusion implant 2300a and 2300b are adjacent to each other and are touching. In this manner, two spinal fusion implants 2300a and 2300b are implanted within the interspace D and engage the bone of the adjacent vertebrae V without exceeding the width of the spinal column. It is appreciated that there are other ways that two spinal implants can have complimentary shapes and that they can be inserted by linear advancement through a single (both at once) or dual outer sleeve having intradiscal extended members for stabilization, distraction, and/or to effect lordosis or kyphosis.

While the present invention has been described in detail with regards to the preferred embodiments, it is appreciated that other variations of the present invention may be devised which do not depart from the inventive concept of the present invention. In particular, it is appreciated that the various teachings described in regards to the specific embodiments herein may be combined in a variety of ways such that the features are not limited to the specific embodiments described above.

Each of the features disclosed in the various embodiments and their functional equivalents may be combined in any combination sufficient to achieve the purposes of the present invention as described herein.

What is claimed is:

1. A method for inserting at least one frusto-conical spinal fusion implant made of a material appropriate for human implantation, said implant having bone engaging means for engaging the adjacent vertebrae in a segment of the spinal column, comprising the steps of:
   distracting said adjacent vertebrae and placing said adjacent vertebrae in an angular relationship;
   forming a frusto-conical bore from the anterior or posterior aspect of the spinal column across the distracted disc space between said adjacent vertebrae and into the adjacent vertebrae, said bore being at least in part greater in diameter than the distracted disc space such that some bone is removed from each of the adjacent vertebrae; and
   inserting a frusto-conical spinal fusion implant into said bore.

2. The method of claim 1 in which said bore is greatest in diameter anteriorly and tapering to a lesser diameter posteriorly.

3. The method of claim 1 in which said bore is substantially cylindrical.

4. The method of claim 1 in which said step of forming includes the steps of using a drill having a substantially frusto-conical shaped bone removing portion.

5. The method of claim 1 further comprising the step of inserting a second spinal fusion implant across the disc space so as to engage each of the adjacent vertebrae, said second implant being side by side and adjacent to said first implant.

6. The method of claim 5 further comprising the steps of forming a second bore across the disc space partially overlapping said first bore, the combined width of said first and second bores being less than the sum of the individual diameters of said first and second bores; and inserting said second implant.

7. The method of claim 1 in which the step of forming said bore includes the substep of removing a portion of bone parallel to the vertebral endplates of the adjacent vertebrae.

8. The method of claim 1, wherein the distracting step includes the step of inserting a spinal distractor into the disc space between the adjacent vertebrae to induce angulation to the adjacent vertebrae.

9. The method of claim 8, further comprising the step of positioning a sleeve over said spinal distractor and into contact with the adjacent vertebrae.

10. The method of claim 9, further comprising the step of removing said spinal distractor prior to the step of forming.

11. The method of claim 9, wherein the positioning step includes the step of positioning a sleeve having an extension for insertion into the disc space and for bearing against end plates of the adjacent vertebrae.

12. The method of claim 11, wherein the positioning step includes the sub-step of inducing angulation to the adjacent vertebrae.

13. The method of claim 12, wherein the inducing angulation step includes the step of restoring lordosis to the adjacent vertebrae.

14. The method of claim 12, wherein the inducing angulation step includes the step of restoring kyphosis to the asdjacent vertebrae.

15. The method of claim 9, wherein the forming step includes the sub-step of drilling the bore.

16. The method of claim 15, wherein the forming step further comprises the sub-step of placing a drill having a diameter greater than the disc space through said sleeve prior to the sub-step of drilling.

17. The method of claim 9, wherein the step of inserting includes the sub-step of inserting said implant through said sleeve and into the bore.

18. The method of claim 9, further comprising the step of placing an inner sleeve within said sleeve prior to the step of forming the bore.

19. The method of claim 18, further comprising the step of removing said inner sleeve prior to the step of inserting said implant.

20. The method of claim 1, wherein the forming step includes the sub-step of milling the bore.

21. The method of claim 1, further comprising the step of loading said implant with fusion promoting material prior to the step of inserting.

22. The method of claim 1, further comprising the step of loading said implant with osteogenic material prior to the step of inserting.

23. The method of claim 1, further comprising the step of coating said implant with bone morphogenic proteins prior to the step of inserting.

24. The method of claim 1, wherein the step of inserting includes inserting an implant containing a fusion promoting substance.

25. The method of claim 1, wherein the step of inserting includes inserting an implant comprising a fusion promoting substance.

26. The method of claim 1, wherein the step of inserting includes inserting an implant comprising a bone ingrowth surface.

27. A method for inserting at least one frusto-conical spinal fusion implant made of a material appropriate for human implantation, said implant having bone engaging means for engaging the adjacent vertebrae in a segment of the spinal column, comprising the steps of:
   distracting the adjacent vertebrae;
   forming a bore from the anterior or posterior aspect of the spinal column across the disc space and into the adjacent vertebrae, said bore being at least in part greater in diameter than the disc space between the distracted vertebrae such that some bone is removed from each of the adjacent vertebrae; and
   inserting a frusto-conical spinal fusion implant into said bore.

28. The method of claim 27 in which said bore is generally cylindrical in shape.

29. The method of claim 22 in which said step of forming the step of includes using a drill having a substantially cylindrical shaped bone removing portion.

30. The method of claim 22 further comprising the step of inserting a second spinal fusion implant across the disc space so as to engage each of the adjacent vertebrae, said second implant being side by side and adjacent to said first implant.

31. The method of claim 30 further comprising the steps of forming a second bore across the disc space partially overlapping said first bore, the combined width of said first and second bores being less than the sum of the individual diameters of said first and second bores; and inserting said second spinal fusion implant into said second bore.

32. The method of claim 27 in which the step of forming said bore includes the substep of removing a portion of bone parallel to the endplates of the adjacent vertebrae.

33. The method of claim 27, wherein the distracting step includes the step of inserting a spinal distractor into the disc space between the adjacent vertebrae to induce angulation to the adjacent vertebrae.

34. The method of claim 33, further comprising the step of positioning a sleeve over said spinal distractor and into contact with the adjacent vertebrae.

35. The method of claim 34, further comprising the step of removing said spinal distractor prior to the step of forming.

36. The method of claim 41, wherein the positioning step includes the step of positioning a sleeve having an extension for insertion into the disc space and for bearing against end plates of the adjacent vertebrae.

37. The method of claim 34, wherein the positioning step includes the sub-step of inducing angulation to the adjacent vertebrae.

38. The method of claim 37, wherein the inducing angulation step includes the step of restoring lordosis to the adjacent vertebrae.

39. The method of claim 37, wherein the inducing angulation step includes the step of restoring kyphosis to the adjacent vertebrae.

40. The method of claim 34, wherein the forming step includes the sub-step of drilling the bore.

41. The method of claim 40, wherein the forming step further comprises the sub-step of placing a drill having a diameter greater than the disc space through said sleeve prior to the sub-step of drilling.

42. The method of claim 41, further comprising the step of placing an inner sleeve within said sleeve prior to the step of forming the bore.

43. The method of claim 42, further comprising the step of removing said inner sleeve prior to the step of inserting said implant.

44. The method of claim 34, wherein the step of inserting includes the sub-step of inserting said implant through said sleeve and into the bore.

45. The method of claim 27, wherein the forming step includes the sub-step of milling the bore.

46. The method of claim 22, further comprising the step of loading said implant with fusion promoting material prior to the step of inserting.

47. The method of claim 27, further comprising the step of loading said implant with osteogenic material prior to the step of inserting.

48. The method of claim 27, further comprising the step of coating said implant with bone morphogenic proteins prior to the step of inserting.

49. The method of claim 27, wherein the step of inserting includes inserting an implant containing a fusion promoting substance.

50. The method of claim 27, wherein the step of inserting includes inserting an implant comprising a fusion promoting substance.

51. The method of claim 27, wherein the step of inserting includes inserting an implant comprising a bone ingrowth surface.

52. A method for inserting a spinal implant across a disc space between adjacent vertebrae of a human spine, comprising the steps of:
   distracting said adjacent vertebrae to induce angulation to the adjacent vertebrae;
   forming a bore from the anterior or posterior aspect of the spinal column across the distracted disc space between said adjacent vertebrae and into the adjacent vertebrae, said bore having opposed arcuate portions in an angular relationship to one another along at least a portion of each of the adjacent vertebrae; and
   inserting into said bore said spinal implant having opposed arcuate portions in an angular relationship to one another along the length of said implant and oriented toward the adjacent vertebrae.

53. The method of claim 52, wherein the distracting step includes the step of inserting a spinal distractor into the disc space between the adjacent vertebrae to induce angulation to the adjacent vertebrae.

54. The method of claim 53, further comprising the step of positioning a sleeve over said spinal distractor and into contact with the adjacent vertebrae.

55. The method of claim 52, further comprising the step of removing said spinal distractor prior to the step of forming.

56. The method of claim 54, wherein the positioning step includes the step of positioning a sleeve having an extension for insertion into the disc space and for bearing against end plates of the adjacent vertebrae.

57. The method of claim 56, wherein the positioning step includes the sub-step of inducing angulation to the adjacent vertebrae.

58. The method of claim 57, wherein the inducing angulation step includes the step of restoring lordosis to the adjacent vertebrae.

59. The method of claim 57, wherein the inducing angulation step includes the step of restoring kyphosis.

60. The method of claim 54, wherein the forming step includes the sub-step of drilling the bore.

61. The method of claim 60, wherein the forming step further comprises the sub-step of placing a drill having a diameter greater than the disc space through said sleeve prior to the sub-step of drilling.

62. The method of claim 54, wherein the step of inserting includes the sub-step of inserting said implant through said sleeve and into the bore.

63. The method of claim 54, further comprising the step of placing an inner sleeve within said sleeve prior to the step of forming the bore.

64. The method of claim 63, further comprising the step of removing said inner sleeve prior to the step of inserting said implant.

65. The method of claim 52, wherein the forming step includes the sub-step of milling the bore.

66. The method of claim 52, further comprising the step of loading said implant with fusion promoting material prior to the step of inserting.

67. The method of claim 54, further comprising the step of loading said implant with osteogenic material prior to the step of inserting.

68. The method of claim 52, further comprising the step of coating said implant with bone morphogenic proteins prior to the step of inserting.

69. The method of claim 52, wherein the step of inserting includes inserting an implant containing a fusion promoting substance.

70. The method of claim 52, wherein the step of inserting includes inserting an implant comprising a fusion promoting substance.

71. The method of claim 52, wherein the step of inserting includes inserting an implant comprising a bone ingrowth surface.

72. A method for inserting a spinal implant across a disc space between adjacent vertebrae of a human spine, comprising the steps of:

forming a bore from the anterior or posterior aspect of the spinal column across the disc space and into the adjacent vertebrae, said bore being at least in part greater in diameter than the distracted disc space such that some bone is removed from each of the adjacent vertebrae; and inserting into said bore said spinal implant having opposed arcuate portions oriented toward the adjacent vertebrae, said arcuate portions being in a diverging relationship to one another along the length of said implant sufficient to induce angulation of the vertebrae.

73. The method of claim 72, further comprising the step of distracting the adjacent vertebrae prior to the forming step.

74. The method of claim 73, wherein the distracting step includes the step of inserting a spinal distractor into the disc space between the adjacent vertebrae to induce angulation to the adjacent vertebrae.

75. The method of claim 74, further comprising the step of positioning a sleeve over said spinal distractor and into contact with the adjacent vertebrae.

76. The method of claim 75, further comprising the step of removing said spinal distractor prior to the step of forming.

77. The method of claim 75, wherein the positioning step includes the step of positioning a sleeve having an extension for insertion into the disc space and for bearing against end plates of the adjacent vertebrae.

78. The method of claim 77, wherein the positioning step includes the sub-step of inducing angulation to the adjacent vertebrae.

79. The method of claim 78, wherein the inducing angulation step includes the step of restoring lordosis to the adjacent vertebrae.

80. The method of claim 78, wherein the inducing angulation step includes the step of restoring kyphosis.

81. The method of claim 75, wherein the forming step includes the sub-step of drilling the bore.

82. The method of claim 81, wherein the forming step further comprises the sub-step of placing a drill having a diameter greater than the disc space through said sleeve prior to the sub-step of drilling.

83. The method of claim 75, wherein the step of inserting includes the sub-step of inserting said implant through said sleeve and into the bore.

84. The method of claim 75, further comprising the step of placing an inner sleeve within said sleeve prior to the step of forming the bore.

85. The method of claim 84, further comprising the step of removing said inner sleeve prior to the step of inserting said implant.

86. The method of claim 72, wherein the forming step includes the sub-step of milling the bore.

87. The method of claim 72, further comprising the step of loading said implant with fusion promoting material prior to the step of inserting.

88. The method of claim 72, further comprising the step of loading said implant with osteogenic material prior to the step of inserting.

89. The method of claim 72, further comprising the step of coating said implant with bone morphogenic proteins prior to the step of inserting.

90. The method of claim 72, wherein the step of inserting includes inserting an implant containing a fusion promoting substance.

91. The method of claim 72, wherein the step of inserting includes inserting an implant comprising a fusion promoting substance.

92. The method of claim 72, wherein the step of inserting includes inserting an implant comprising a bone ingrowth surface.

* * * * *

UNITED STATES PATENT AND TRADEMARK OFFICE
CERTIFICATE OF CORRECTION

PATENT NO. : 6,210,412 B1
DATED : April 3, 2001
INVENTOR(S) : Gary Karlin Michelson Page 1 of 1

It is certified that error appears in the above-identified patent and that said Letters Patent is hereby corrected as shown below:

Column 22, claim 14,
Line 3, change "asdjacent" to -- adjacent --;

Column 23, claim 29,
Line 1, change "22" to -- 27 --, and change "said" to -- the --;
Line 2, delete "the step of";

Column 23, claim 30,
Line 1, change "22" to -- 27 --;

Column 24, claim 36,
Line 1, change "41" to -- 34 --;

Column 24, claim 46,
Line 1, change "22" to -- 27 --;

Column 25, claim 55,
Line 1, change "52" to -- 54 --; and

Column 25, claim 67,
Line 1, change "54" to -- 52 --.

Signed and Sealed this

Sixteenth Day of October, 2001

Attest:

NICHOLAS P. GODICI
Attesting Officer
*Acting Director of the United States Patent and Trademark Office*